(12) United States Patent
Advani

(10) Patent No.: US 11,403,651 B2
(45) Date of Patent: Aug. 2, 2022

(54) GENERATING INSIGHTS BASED ON SIGNALS FROM MEASURING DEVICE

(71) Applicant: Georama, Inc., Chicago, IL (US)

(72) Inventor: Nihal Advani, Chicago, IL (US)

(73) Assignee: Georama, Inc., Chicago, IL (US)

( * ) Notice: Subject to any disclaimer, the term of this patent is extended or adjusted under 35 U.S.C. 154(b) by 0 days.

(21) Appl. No.: 17/535,541

(22) Filed: Nov. 24, 2021

(65) Prior Publication Data

US 2022/0114604 A1    Apr. 14, 2022

Related U.S. Application Data

(63) Continuation of application No. 17/175,576, filed on Feb. 12, 2021, now Pat. No. 11,195,189.

(Continued)

(51) Int. Cl.
*G06Q 20/02*        (2012.01)
*G06Q 30/02*        (2012.01)
(Continued)

(52) U.S. Cl.
CPC ......... *G06Q 30/0201* (2013.01); *G01D 21/02* (2013.01); *G06F 16/215* (2019.01); *H04L 12/2825* (2013.01); *H04L 2012/285* (2013.01)

(58) Field of Classification Search
CPC . H04L 63/0272; H04L 45/22; H04L 12/4641; H04L 12/4633; H04L 45/124; H04L 45/04; H04L 47/125; H04L 12/44; H04L 45/121; H04L 2212/00; H04L 12/2825; H04L 2012/285; G06Q 30/0201; G01D 21/02; G06F 16/215
See application file for complete search history.

(56) References Cited

U.S. PATENT DOCUMENTS 9,736,554 B2   8/2017   Hershberger et al.
11,195,189 B1  12/2021  Advani
(Continued)

FOREIGN PATENT DOCUMENTS

KR   10-2001-0023036   3/2001
KR   10-1712432        3/2017

OTHER PUBLICATIONS

International Search Report and Written Opinion in International Appln. No. PCT/US2021/054257, dated Feb. 4, 2022, 10 pages.

*Primary Examiner* — Dady Chery
(74) *Attorney, Agent, or Firm* — Fish & Richardson P.C.

(57) ABSTRACT

A system is described that generates insights on the consumption or usage behavior of a product by analyzing the real-time usage of the product by one or more users. The product is placed on the measuring device for continuous monitoring of the usage of the product by those one or more users in real-time. The measuring device includes a sensor unit that generates weigh data, motion data, location data, and time consumed data of the product and transmits to a computing device. A communication device records the consumption or usage of the product by a user, along with feedback from the user. The computing device generates insights based on the sensed data generated by the measuring device, and recording and feedback at the communication device. The computing device generates reports—one for the user, and one for a merchant of the product and/or similar products—including respective insights.

18 Claims, 26 Drawing Sheets

Related U.S. Application Data

(60) Provisional application No. 63/089,956, filed on Oct. 9, 2020.

(51) Int. Cl.
    *G01D 21/02*     (2006.01)
    *H04L 12/28*     (2006.01)
    *G06F 16/215*     (2019.01)

(56) References Cited

U.S. PATENT DOCUMENTS

| | | |
|---|---|---|
| 2003/0096610 A1 | 5/2003 | Courtney et al. |
| 2012/0047022 A1 | 2/2012 | Shamim et al. |
| 2016/0028608 A1 | 1/2016 | Dasgupta et al. |
| 2017/0208493 A1 | 7/2017 | Masson et al. |
| 2019/0156394 A1* | 5/2019 | Karmakar ............ G06Q 10/087 |
| 2019/0296931 A1* | 9/2019 | Apte .................... H04W 4/029 |
| 2019/0324434 A1* | 10/2019 | Celia .................. G05B 23/0283 |
| 2020/0285855 A1* | 9/2020 | Brebner ............. G06K 9/00536 |

* cited by examiner

SEARCH FOR SESSIONS

| GETTING TO KNOW YOU | YOUR CURRENT PRODUCT(S) | CLEANING VIDEO | SURFACE CLEANING SURVEY |
|---|---|---|---|
| PARTICIPANT NAME: JOHN C | PARTICIPANT NAME: JOHN C | PARTICIPANT NAME: JANE P | PARTICIPANT NAME: AUSTIN M |
| CHICAGO, UNITED STATES SEP 2 2020, 06:09 AM STATUS: COMPLETED | CHICAGO, UNITED STATES SEP 1 2020, 11:34 AM STATUS: COMPLETED | PALO ALTO, UNITED STATES SEP 1 2020, 10:39 AM STATUS: COMPLETED | SAN FRANCISCO, UNITED STATES SEP 1 2020, 07:36 AM STATUS: COMPLETED |

| DISHWASHER ACTIVITY | KITCHEN TAP ACTIVITY | YOUR DISHWASHING HABITS | GETTING TO KNOW YOU |
|---|---|---|---|
| PARTICIPANT NAME: AUSTIN M | PARTICIPANT NAME: AUSTIN M | PARTICIPANT NAME: AUSTIN M | PARTICIPANT NAME: AUSTIN M |
| SAN FRANCISCO, UNITED STATES AUG 30 2020, 11:09 AM STATUS: COMPLETED | SAN FRANCISCO, UNITED STATES AYG 30 2020, 08:09 AM STATUS: COMPLETED | SAN FRANCISCO, UNITED STATES AUG 30 2020, 07:20 AM STATUS: COMPLETED | SAN FRANCISCO, UNITED STATES AUG 30 2020, 06:09 AM STATUS: COMPLETED |

FIG. 8

TASKS / QUESTIONS

6. PRODUCT 1 – PLEASE TAKE THE PRODUCT YOU USE FOR DISHWASHING LIQUID AND POINT YOUR CAMERA TO THE BARCODE. IF IT DOESN'T AUTOMATICALLY DETECT THEN USE THE CAMERA BUTTON TO TAKE A PICTURE.

| BARCODE | BARCODE_TYPE | MANUFACTURER | CATEGORY | BRAND |
|---|---|---|---|---|
| 4284221066659 | HDC | [NAME OF MANUFACTURER] | HAND DISH CLEANERS 10.0 | FAIRY |

| UPC_DETAIL | BASE_SIZE | | SUBBRAND | MAIN_CATEGORY | COLLECTION |
|---|---|---|---|---|---|
| +PRO2 PGPPL LIQ SS 500ML | 1190ML | | CHEERS | HAND DISH CLEANERS | |

| GROUP_SCENT_BENEFIT | | FORM |
|---|---|---|
| | | LIQUID/GEL |

FIG. 9

|  | WEEK-1 (ENDING 06/05/20) | WEEK-2 (ENDING 06/12/20) | WEEK-3 (ENDING 06/17/20) | WEEK-4 (ENDING 06/26/20) | WEEK-5 (ENDING 07/03/20) | WEEK-6 (ENDING 07/10/20) | WEEK-7 (ENDING 07/17/20) | WEEK-8 (ENDING 07/24/20) | WEEK-9 (ENDING 07/31/20) |
|---|---|---|---|---|---|---|---|---|---|
| AVERAGE WEEKLY CONSUMPTION (FRIDAY TO FRIDAY, IN GRAMS) | - | 93.80 | 105.25 | 91.33 | 97.86 | 89.75 | 99.00 | 97.82 | 103.82 |
| AVERAGE WEEKLY CONSUMPTION INDEX WEEK PRIOR | - | - | 112.21 | 86.77 | 107.15 | 91.71 | 110.31 | 98.81 | 100.13 |
| AVERAGE WEEKEND CONSUMPTION (GRAMS PER DAY) | - | 21.88 | 14.56 | 17.66 | 15.80 | 14.85 | 17.11 | 12.80 | 14.97 |
| AVERAGE WEEKDAY CONSUMPTION (GRAMS PER DAY) | - | 12.53 | 14.82 | 14.19 | 15.01 | 15.47 | 15.10 | 13.43 | 18.20 |
| # OF WEIGH-INS (SAME BOTTLE) | 75 | 61 | 76 | 72 | 72 | 75 | 82 | 78 | 72 |
| # OF WEIGH-INS (NEW BOTTLE) | - | 30 | 13 | 25 | 20 | 23 | 13 | 13 | 20 |
| # OF OOS (OUT OF STOCK) | - | - | - | - | - | - | - | - | - |
| # OF WEIGH-INS (TOTAL) | 75 | 93 | 90 | 98 | 98 | 102 | 98 | 96 | 98 |

FIG. 11

TASKS/QUESTIONS

11. LETS SWITCH TO PRODUCT 2 – PLEASE TAKE THE PRODUCT YOU USE FOR FLOOR CLEANER AND POINT YOUR CAMERA TO THE BARCODE. IF IT DOESN'T AUTOMATICALLY DETECT THEN USE THE CAMERA BUTTON TO TAKE A PICTURE.

12. PRODUCT 2 – NOW PLEASE PLACE THE SAME PRODDUCT FOR FLOOR CLEANER ON THE KITCHEN SCALE, WAIT FOR THE READING TO SHOW, AND TAKE A PICTURE SO THAT WE CAN SEE THE PRODUCT AND THE MEMBER ON THE SCALE.

13. PRODUCT 2 – PLEASE ENTER THE WEIGHT (NUMBER) OF YOUR FLOOR CLEANER. MAKE SURE YOU ENTER THE COMPLETE NUMBER INCLUDING THE DECIMAL POINT AND ANY NUMBER THAT FOLLOW.

749

14. LETS SWITCH TO PRODUCT 3 – PLEASE TAKE THE PRODUCT YOU USE FOR ALL PURPOSE CLEANING SPRAY AND POINT YOUR CAMERA TO THE BARCODE. IF IT DOESN'T AUTOMATICALLY DETECT THEN USE THE CAMERA BUTTON TO TAKE A PICTURE.

| CUSTOM REPORTS | QUANTITATIVE CHARTS | | | | | | |
|---|---|---|---|---|---|---|---|
| SEARCH FOR RESPONSES | | WEEKLY SCORECARD | CATEGORY DASHBOARD | WEIGH-IN DASHBOARD | | | | |
| | | DISHWASHING LIQUID | DISHWASHER DETERGENT PODS/PACS/SINGLE-DOSE | FLOOR CLEANER | ALL PURPOSE CLEANING SPRAY |
| PARTICIPANT | SESSION | DATE | FILTER DISHWASHING LIQUID | FILTER DISHWASHING DETERGENT | FILTER FLOOR CLEANER | FILTER ALL PURPOSE CLEANING |
| JANE DOE | FRIDAY JUNE 5 WEIGH IN | 2020-06-05 | 361 | 428 | 668 | 780 |
| JANE DOE | SUNDAY JUNE 7 WEIGH IN | 2020-06-07 | 354 | 409 | 658 | 766 |
| JANE DOE | FRIDAY JUNE 12 WEIGH IN | 2020-06-13 | 336 | 341 | 654 | 761 |
| JANE DOE | SUNDAY JUNE 14 WEIGH IN | 2020-06-14 | 0304 | 0322 | 0651 | 0761 |
| JANE DOE | FRIDAY JUNE 19 WEIGH IN | 2020-06-19 | 0256 | 0291 | 0652 | 0757 |
| JANE DOE | SUNDAY JUNE 21 WEIGH IN | 2020-06-21 | 0252 | 0273 | 0635 | 0759 |
| JANE DOE | FRIDAY JUNE 26 WEIGH IN | 2020-06-26 | 0230 | 0220 | 0633 | 0746 |
| JANE DOE | SUNDAY JUNE 28 WEIGH IN | 2020-06-28 | 0222 | 0185 | 0634 | 0746 |

FIG. 14

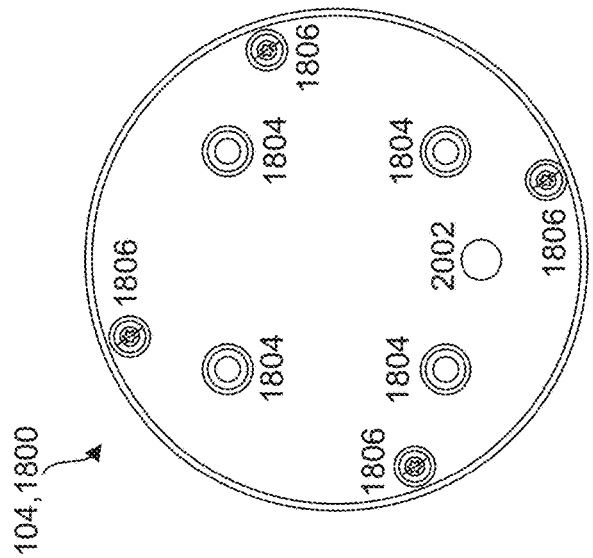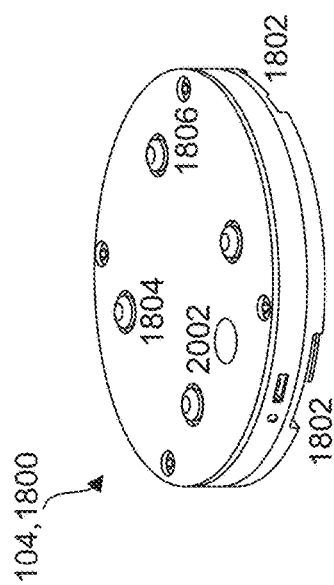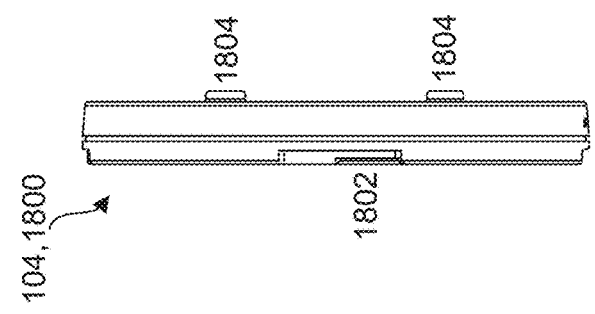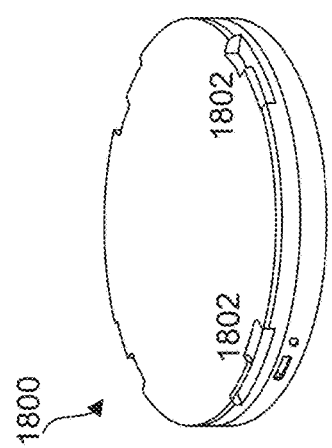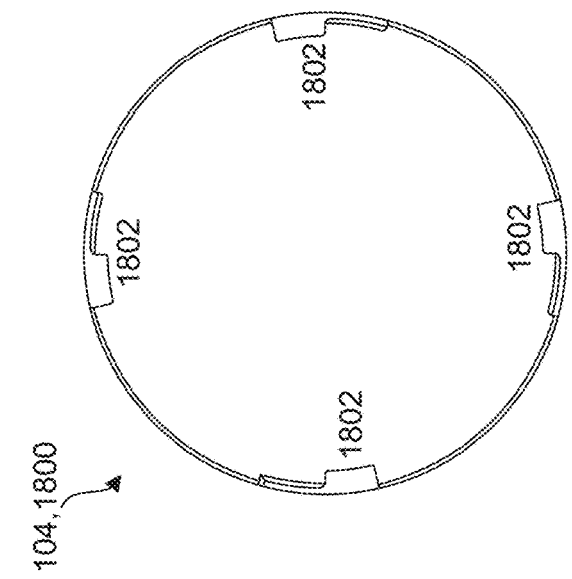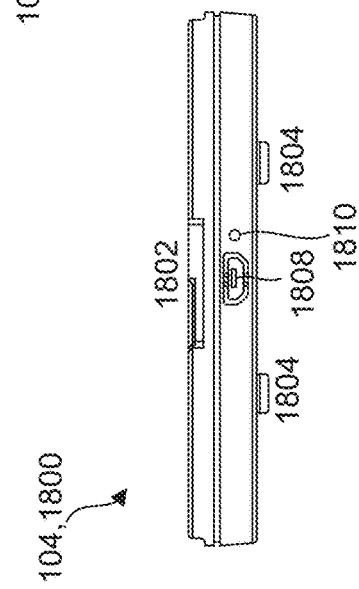

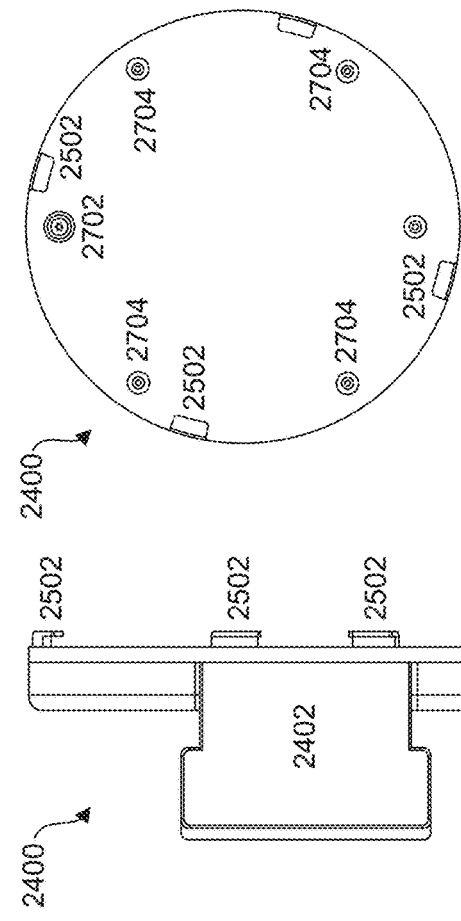
FIG. 24
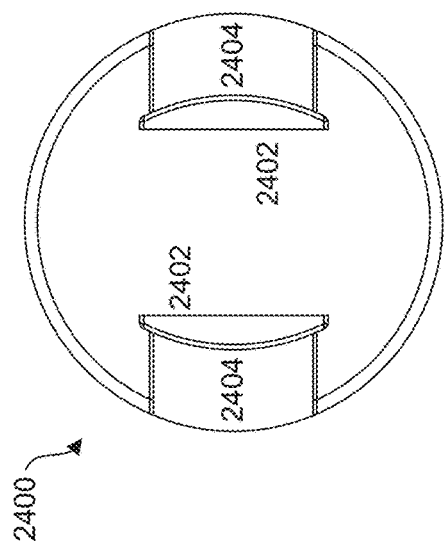
FIG. 25
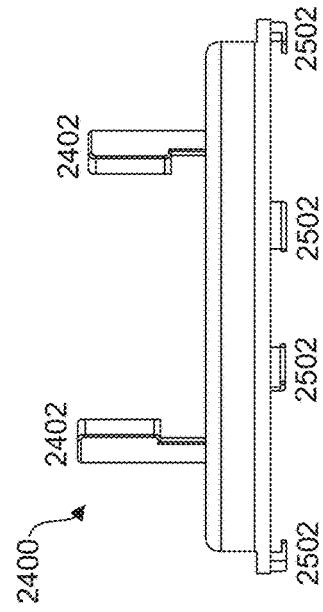
FIG. 26
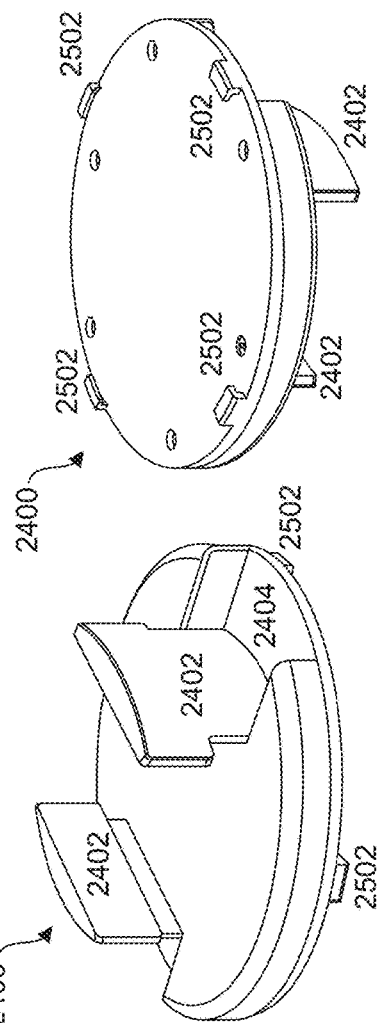
FIG. 27
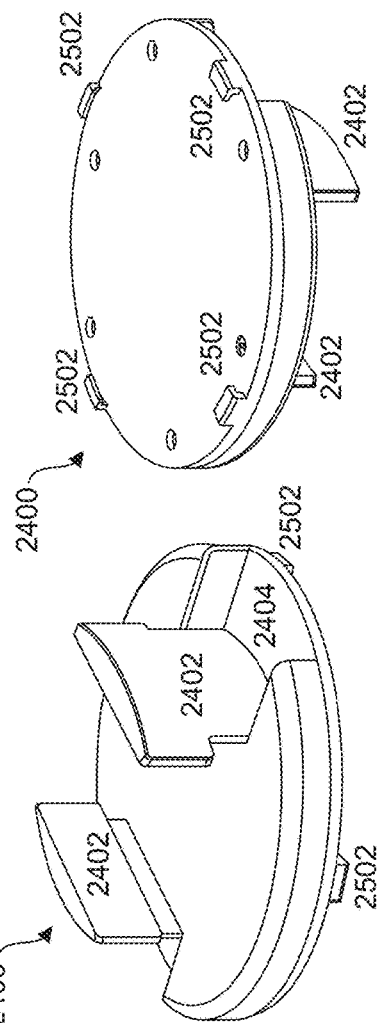
FIG. 28
FIG. 29

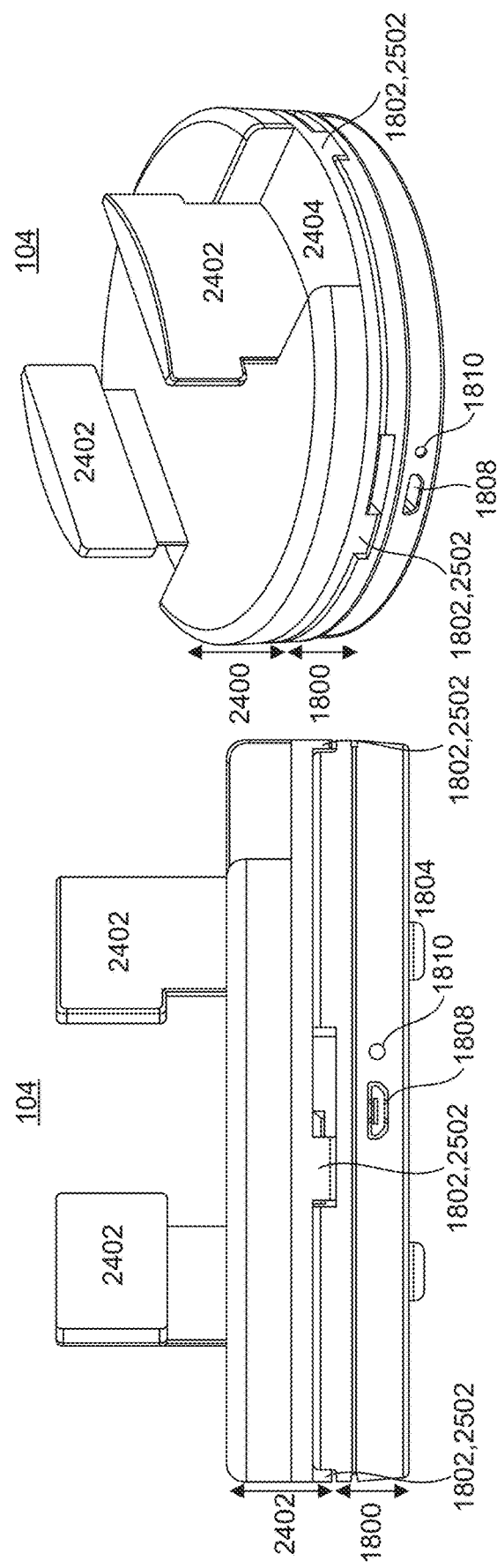

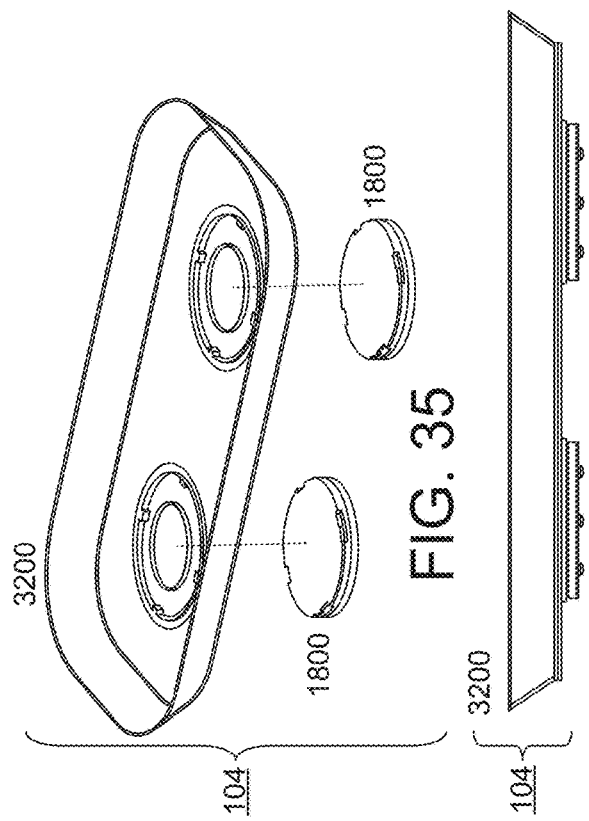
FIG. 35
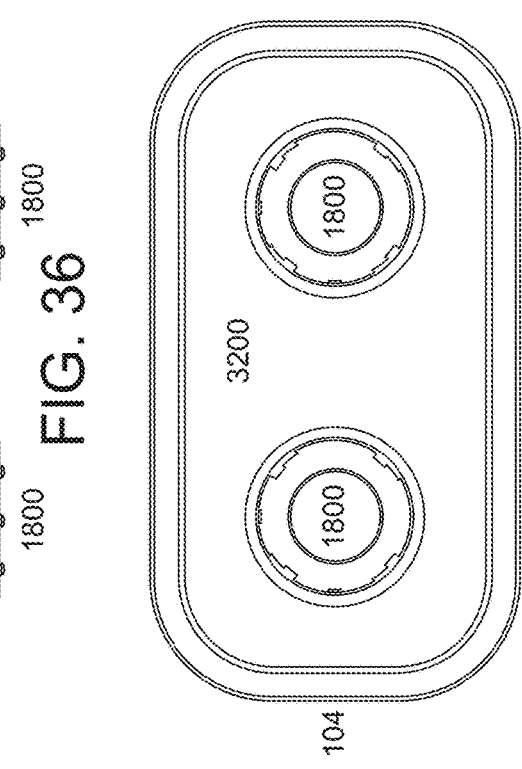
FIG. 36
FIG. 37
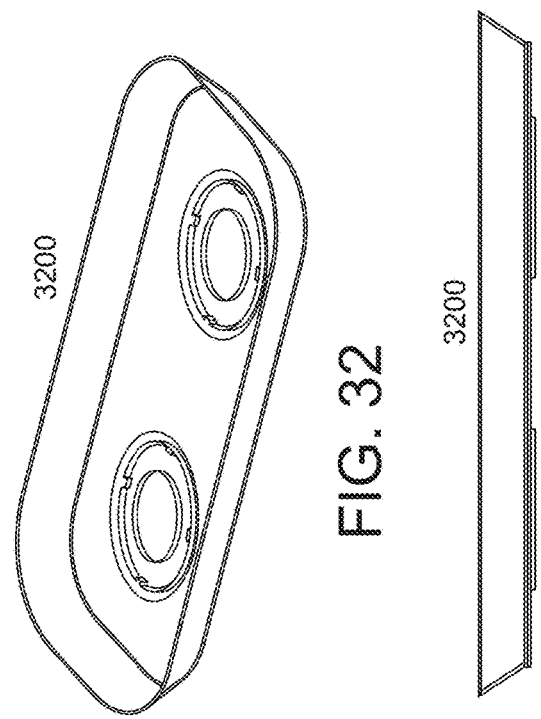
FIG. 32
FIG. 33
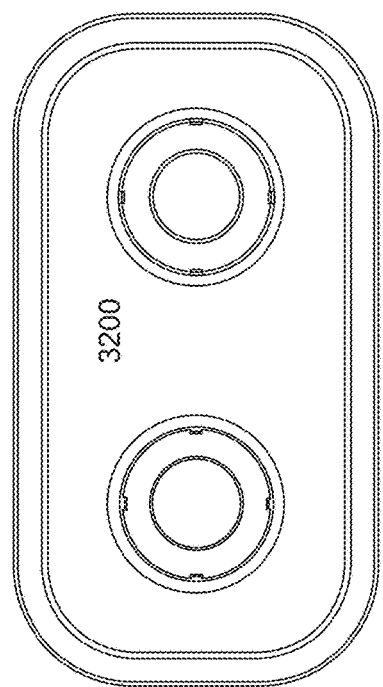
FIG. 34

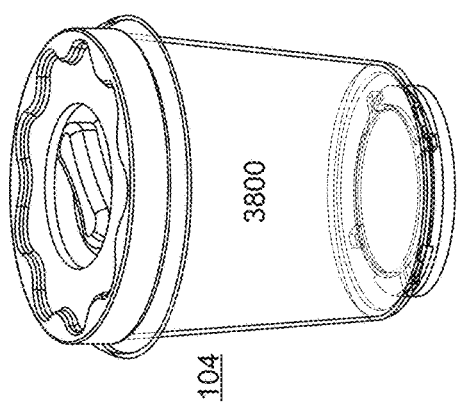
FIG. 39
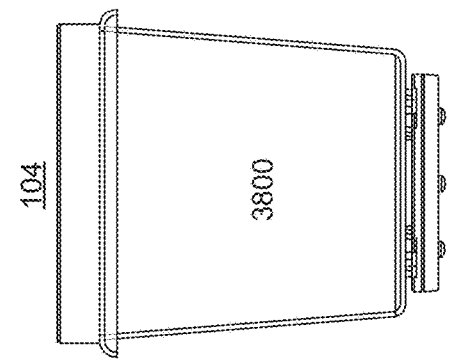
FIG. 41
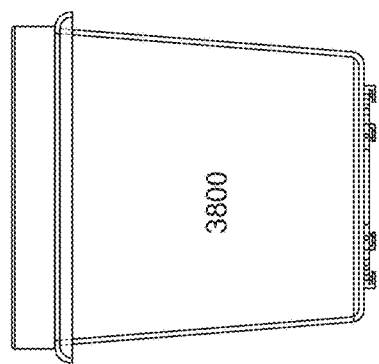
FIG. 40
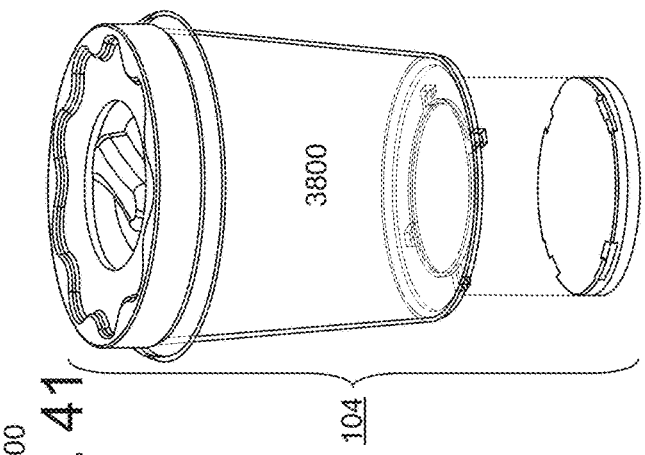
FIG. 42
FIG. 38

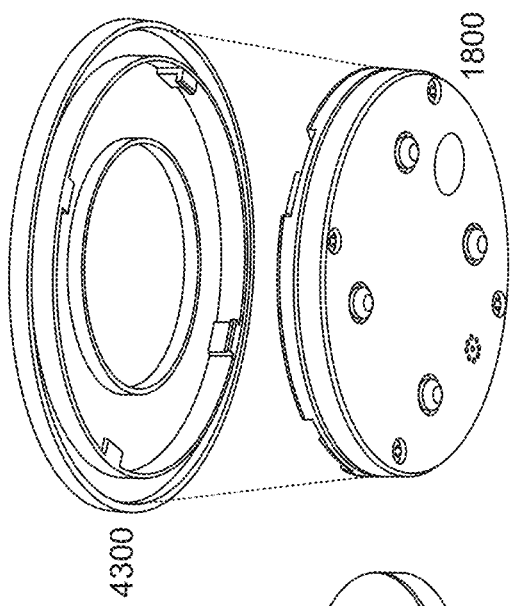
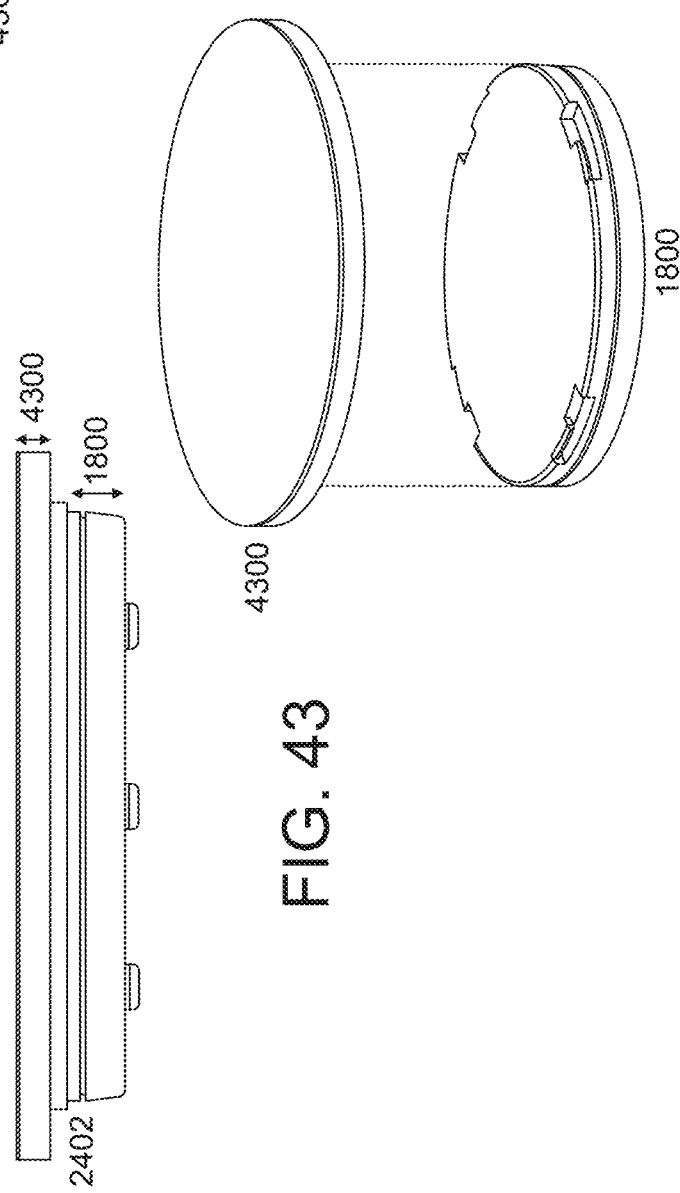
FIG. 45
FIG. 44
FIG. 43

GENERATING INSIGHTS BASED ON SIGNALS FROM MEASURING DEVICE

RELATED APPLICATIONS

This application is a continuation of U.S. application Ser. No. 17/175,576 filed on Feb. 12, 2021, which claims priority to U.S. Provisional Patent Application No. 63/089,956, filed on Oct. 9, 2020. The disclosures of the prior applications are considered part of and are incorporated by reference in the disclosure of this application.

TECHNICAL FIELD

The subject matter described herein relates to various implementations of a device configured to detect consumption or usage of a product, and generation of insights based on the detected consumption or usage.

BACKGROUND

Merchants (e.g. manufacturers, distributors, retailers, and/or the like) can benefit from identifying consumption behavior that indicates how users (e.g. consumers) interact with a product (e.g. how users purchase, perceive, and/or either consume or use the product). For example, a merchant can interpret consumption behavior to understand the needs, desires, habits, patterns, preferences, and problems of users. Based on the understanding of the needs, desires, habits, patterns, preferences, and problems of the users, the merchant may make several changes and identifications to maximize sales and customer satisfaction. Such changes include modifications to: where the product is placed within various distribution channels, structural details or other features of the product, packaging of the product, content of messaging in a digital component related to the product, mode (e.g., email or text message) of transmitting the digital component to respective users, timeline for launching new products, and/or the like. Such identifications include identifications of new opportunities, new segments of target audience, geographies for various business processes (e.g. marketing, sales, manufacturing), and/or the like.

However, the traditional techniques for collecting and understanding consumption or usage behavior may not be optimal. For instance, while merchants have a significant amount of data on the purchase behavior of consumers based on retailer data and/or their own sales data, they typically have little to no idea about the actual consumption or usage data of those products and/or actual consumption or usage behavior of consumers (i.e. users) using those products after the products have been purchased by consumers. In some instances, merchants may—either themselves or through other companies—conduct ad-hoc research studies or tap into syndicated research data to try to determine consumption behavior. However, such studies and research activities are ineffective for many reasons. First, such studies typically provide some indication of consumption behavior during a particular point in time rather than over a long period of time that can better indicate consumer behavior. Second, such studies and research activities generate results based on data of usage informed or claimed by the consumers instead of being based on actual consumption, which may not match what the user informs or claims, and thus such results can be inaccurate. Third, some such studies may involve a company representative visiting homes or other locations of the users to check on usage, but such practices may be unduly burdensome, cost-prohibitive, discouraged by the users, and also only provide infrequent data on what products were finished (fully used/consumed) but not when, how much, how often, and where they were consumed.

Due to such ineffectiveness, such conventional studies and research activities do not allow the merchants to obtain deep, authentic, and accurate insights into consumption or usage data of products and/or consumer behavior regarding consumption or usage of products by the consumers or users of those products. For example, the merchants are traditionally unable to obtain insights (a) based on actual consumption or use of the product, (b) in an automatic and passive manner, (c) in a fast or timely manner, such as in real-time, (d) that are scalable for large amounts of users, regions, categories, markets, (e) that are ongoing over the life of the product, or a long period of time such as several weeks, months, or years, (f) that are presented in a clear easy-to-comprehend manner. This ineffectiveness of the traditional techniques for collecting and understanding consumption behavior prevents those merchants from providing effectively targeted recommendations, advertisements, promotions, or messaging to the consumers or users, and also hinders the ability of the merchants to develop new products that are effective for those, and/or similar, consumers or users.

SUMMARY

A system is described that cures at least the above-noted deficiencies of the traditional techniques for collecting and understanding consumption or usage behavior while attaining many advantages. In some implementations, the system includes a measuring device that can measure (i.e. detect) consumption of a product by a user. The product can be any product that is consumed by a user, such as food products, drugs (e.g. medications), drinks, cleaning supplies, products for hygiene, or any other product that can be used or consumed by the user. The consumption of the product, as measured by the measuring device, over a period of time can indicate consumption behavior of the user with respect to that product. The measuring device can be configured to be coupled—physically or communicatively over a communication network—to the product. In some examples, the measuring device can be in the form of a coaster, a tray, a sleeve (which can be configured to encompass sides of a container such as a glass or a bottle), a container (e.g. can), an electronic device such as a remote or electronic button, or any other accessory. The consumer or user can record, on a communication device, a video showing how they consume or use the product along with a feedback and/or explanation provided by the consumer while the consumer or user consumes or uses the product.

The measuring device and the communication device can be connected to a backend server, which can generate insights based on the measured consumption. The backend server can generate recommendations based on the data received from the measuring device and the communication device. Some of the insights and the recommendations can be generated specifically for the user, and some of the insights and the recommendations can be generated specifically for the merchant. The insights and/or recommendations specific to the user can be provided to a communication device of the user, and the insights and/or recommendations specific to the entity can be provided to a client device of the merchant. In some examples, the device may also output the recommendations (e.g. display the recommendations on a graphical user interface, generate audio of recommendations output via a speaker on the device, and/or the like). In additional examples, the backend server and/or the device may send the recommendations to the user via any other channel, such as electronic mail, short messaging service (SMS), social media message, or the like.

In one aspect, a method is described that includes one or more of the following. A computing device can receive, from a hub measuring device of a plurality of measuring devices that are configured to be coupled to a product and are arranged according to a hub and spoke architecture comprising the hub measuring device and a plurality of spoke measuring devices coupled to the hub measuring device, measurement indicating consumption or usage of the product by a user. The computing device can generate an output comprising a plurality of insights based on the measurement.

In some implementations, one or more of the following can additionally be additionally implemented either individually or in any feasible combination. The computing device can generate a report comprising at least some of the plurality of insights, wherein the report can be specific to one or more merchants of the product. The computing device can transmit the report to a client device. In certain implementations, the computing device can generate a report including at least some of the plurality of insights, wherein the report can be specific to the user. The computing device can transmit the report to a communication device of the user.

The receiving of the measurement from the hub measuring device can include receiving the measurement from a communication module of the hub measuring device. The communication module can receive sensed data from a sensor module of each active measuring device among the plurality of measuring devices. The sensor module can include a motion sensor, a weight sensor, a location sensor, and a time-clock. The sensed data for each active measuring device can be used to generate the measurement. The generating of the measurement can include removing, from the sensed data, one or more of duplicative data, inconsistent data, a null value, data collected when an error was reported during sensing of the sensed data by the sensor module to obtain the measurement. The sensor module can have a form of a capsule configured to be inserted into different forms of measuring devices.

The computing device can receive, from a smart device, data indicating an activity indicating a consumption or usage of the activity. The computing device can activate a measuring device of the plurality of measuring devices that is available and geographically nearest to the smart device to receive additional measurement indicating further consumption or usage of the product by the user. The smart device can include an appliance wherein the activity comprises opening or closing of at least a portion of the appliance. The appliance can be one of a smart fridge, smart trashcan, a smart cabinet, a smart sink, or a smart washer.

The computing device can receive the measurement from the hub measuring device of the plurality of measuring devices after the hub measuring device has been activated by way of activating an electronic switch. The computing device can receive the measurement from the hub measuring device in real-time. In some implementations, the computing device can receive the measurement from the hub measuring device at programmed intervals of time.

At least one measuring device of the plurality of measuring devices can have a form of a coaster, a tray, or a container. Each measuring device of the plurality of measuring devices can include a hardware module within which electrical circuitry of measuring device resides. The hardware module can be configured to be placed in any of the coaster, the tray, or the container.

Each measuring device of the plurality of measuring devices can be configured to be coupled to the product physically or communicatively over a communication network.

A measuring device of the plurality of measuring devices can identify the user. The receiving of the measurement can occur in response to the identifying of the user.

The computing device can identify content to be output to the user based on the insights. The output can include digital content to be output on an application of a communication device of the user. The application can be a web browser or a native application installed on the communication device.

The computing device can be coupled to the hub measuring device by way of a first communication network. The hub measuring device can be coupled to the plurality of spoke measuring devices by way of a second communication network that is different from the first communication network. At least some spoke measuring devices are coupled to other spoke measuring devices by way of the second communication network.

At least one measuring device of the plurality of measuring devices has the form of a coaster. The coaster is configured to be coupled to an apparatus having a movable sleeve to hold the product.

In another aspect, one or more non-transitory computer program products are described that can store instructions that, when executed by at least one programmable processor, cause the at least one programmable processor to perform operations comprising: receiving, by a computing device from a hub measuring device of a plurality of measuring devices that are configured to be coupled to a product and are arranged according to a hub and spoke architecture comprising the hub measuring device and a plurality of spoke measuring devices coupled to the hub measuring device, measurement indicating consumption or usage of the product by a user; and generating, by the computing device, an output comprising a plurality of insights based on the measurement.

In yet another aspect, a computing device is described that includes at least one programmable processor, and a machine-readable medium storing instructions that, when executed by the at least one processor, cause the at least one programmable processor to perform operations comprising: receiving, from a hub measuring device of a plurality of measuring devices that are configured to be coupled to a product and are arranged according to a hub and spoke architecture comprising the hub measuring device and a plurality of spoke measuring devices coupled to the hub measuring device, measurement indicating consumption or usage of the product by a user; and generating an output comprising a plurality of insights based on the measurement.

Related systems, devices, methods, non-transitory computer program products, processors, machine readable media, and articles of manufacture are within the scope of this disclosure.

The subject matter described herein provides many advantages. For example, the systems and techniques described herein can allow merchants to obtain deep, authentic, and accurate insights about consumption or usage data of products and/or consumer behavior regarding consumption or usage of one or more products by the consumers or users of those one or more products. For example, such systems and techniques allow the merchants to obtain insights (a) based on actual consumption or use of the product, (b) in an automatic and passive manner, (c) in a fast or timely manner, such as in real-time, (d) that are scalable for large amounts of users, regions, categories, markets, (e) that are ongoing over the life of the product, or a long period of time such as several weeks, months, or years, (f) that are presented in a clear easy-to-comprehend manner. Effectiveness of the systems and techniques described herein for collection and understanding of consumption behavior enables those merchants to provide accurately targeted recommendations, advertisements, promotions, or messaging to the consumers or users, and also allows the merchants to develop new products that are effective for those, and/or similar, consumers or users.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

FIG. 8 illustrates an exemplary view of a graphical user interface of the computing device.

FIG. 9 illustrates an exemplary view of a graphical user interface of the computing device.

FIG. 11 is a graphical representation of a report that depicts average weekly consumption, average weekend consumption, and average weekday consumption of the product.

FIG. 12 illustrates an exemplary view of a graphical user interface of the client device.

FIG. 14 is a graphical representation of a report that depicts weekly consumption of the one or more products by the user.

FIGS. 18-23 illustrate different views of an example of a measuring device in the form of a coaster.

FIGS. 24-29 illustrate different views of an apparatus that forms the sleeve of a measuring device and that is configured to be attached to a coaster to form the measuring device.

FIGS. 30 and 31 illustrate different views of a measuring device where the apparatus of FIGS. 24-29 is attached to a coaster (e.g. coaster of FIGS. 18-23).

FIGS. 32-34 illustrate different views of a tray of a particular measuring device that is made operable by coupling (e.g. attaching) the tray with one or more coasters.

FIGS. 35-37 illustrate different views of the measuring device formed by combining the tray of FIGS. 32-34 with coasters (one example of which is shown in FIGS. 18-23).

FIGS. 38 and 39 illustrate different views of a container of a particular measuring device that is made operable by coupling (e.g. attaching) the container with a coaster (one example of which is shown in FIGS. 18-23).

FIGS. 40-42 illustrate different views of the measuring device formed, or being formed, by combining the container of FIGS. 38 and 39 with a coaster (one example of which is shown in FIGS. 18-23).

FIGS. 43-45 illustrate different views of an adapter configured to modify a form factor of the measuring device.

Like reference symbols in various drawings indicate like elements.

DETAILED DESCRIPTION

General Overview

A system is described that can generate insights and recommendations based on consumption or usage of one or more products by one or more users. The system includes a measuring device to measure characteristics (e.g. weight, motion, location, time of consumption or usage, and/or the like) of a product, a communication device to provide instructions to a user and receive feedback while the user consumes or uses the product, a computing device to perform machine learning on data received from the measuring device and the communication device to generate insights and recommendations that are respectively specific to user and/or entity (e.g. merchant of the product), and a client device configured to be operated by the entity. The computing device transmits the insights and/or recommendations for the user to the communication device, and the insights and/or recommendations for the entity to the client device. Various architectural modifications are possible, as explained in greater detail below.

The insights or recommendations for the consumer or user can help the consumer or user modify consumption or usage habits to improve the quality of life. The insights or recommendations for the entity can help the entity assess their product portfolio and campaigns, create new products, and make modifications to existing products, content of products, size of products, manufacturing processes, advertising campaigns, distribution channels, and/or any other purpose.

Example Architecture of System that Generates Insights and Recommendations

Figure 1:
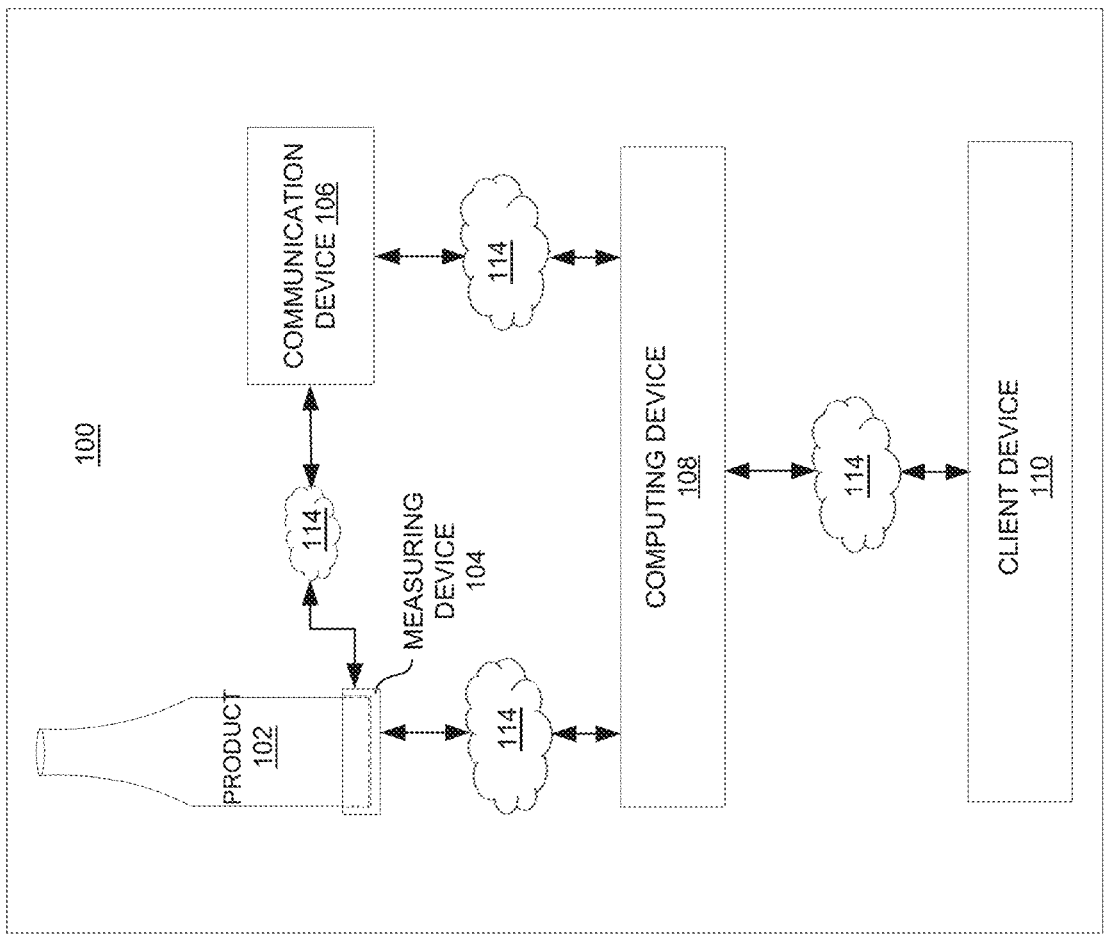
FIG. 1 illustrates a system view of a system that generates insights on the behavior of consumption or usage of a product by a user.

FIG. 1 illustrates a system 100 that generates insights on behavior of usage or consumption of a product 102 by a user, in accordance with some implementations described herein.

The product 102 may include any tangible good that can be consumed or used. For example, the product 102 can include household cleaning items, consumer packaged goods, food and beverages, and/or the like. The system 100 can include a measuring device 104, a communication device 106, a computing device 108, a client device 110 and a communication network 114. The measuring device 104 can measure (e.g. sense or detect) consumption or usage of the product 102 by the user.

The communication device 106 can be a computing system (e.g. phone, tablet computer, phablet computer, a laptop, or the like) configured to be operated by the consumer or user of the product 102, can record data (e.g. video, photo or audio) of a consumer or user while consuming or using the product 102 or other related activities such as opening or storing the product 102. The computing device 108 can receive data on the measurements of consumption or usage from the measuring device 104 and/or the data of consumption or usage from the communication device 106, and can use those data to generate (a) insights based on the measured consumption or usage of the product 102 and/or (b) recommendations based on the insights. Each of the insights and the recommendations can be generated for (i) an entity that deals with the product 102, such as a merchant (e.g. manufacturers, distributors, retailers, and/or the like) of the product 102, or (ii) the user who consumes or uses the product. The client device 110 can be a computing system (e.g. computer) configured to be operated by a merchant (e.g. manufacturers, distributors, retailers, and/or the like) of the product 102. The computing device 108 can transmit the insights and/or the recommendations specific to the user over the communication network 114 to the communication device 106, and can transmit the insights and/or the recommendations specific to the entity over the communication network 114 to the client device 110.

Measuring Device, Communication Device, and Collection of Data Used for Insights The measuring device 104, which measures (e.g. detects or senses) the consumption or usage of the produce 102, can be coupled to the product 102.

Coupling Details for Coupling Measuring Device with Product

The coupling can be physical, or remote over a communication network. The physical coupling can involve the measuring device 104 being either simply placed below the product 102 or attached (e.g. affixed by way of gluing, knitting or threading, welding, twisting and turning multiple components, pressing components with respect to each other or toward each other, and/or any other one or more attachment mechanisms) to any suitable area on a packaging (e.g. housing, or any exterior boundary) of the product 102. In some instances, the measuring device 104 can have separate components such that a first set of one or more components are placed below the product 102 and a second set (e.g. another different set) of one or more components is attached (e.g. affixed) to any suitable area on a packaging of the product 102.

The area, portion or location on the product 102 to which the measuring device 104 is coupled can vary depending on the features (e.g. properties or characteristics) of the product, such as the form of product 102 (e.g. solid, liquid, or gas), shape of the product 102, volume of the product, cohesive properties of the product 102, adhesive properties of the product 102, surface tension of the product 102, capillary action of the product 102, pressure of the product 102, temperature of the product 102 when the product is to be used and/or stored, viscosity of the product 102, and/or the like. For example, in some implementations, the features may require that the product 102 should be as close as possible to the measuring device 104 so that the measuring device 104 can make accurate measurements, and in such case the location of coupling on the measuring device 104 may be chosen accordingly. In other implementations, the features may require that the product 102 should be as far as possible to the measuring device 104 so that the features do not interfere with the measuring functionality or related components within the measuring device 104, and in such case the location of coupling on the measuring device 104 may be chosen accordingly.

To physically couple the product 102 and the measuring device 104, the measuring device 104 can be integrated with, or attached to, a suitable location within the product 102 by way of gluing, knitting or threading, welding, magnetic attachment, fastening, taping, any other mechanical way (e.g. moving, twisting and turning, or pressing two components with respect to each other so they couple), and/or any other one or more attachment mechanisms. In cases where the attachment requires combining of two or more separate components, any of the product 102 and the measuring device 104 may include some or all of those components, in respective implementations. For example, the magnetic attachment may involve a metallic strip affixed to the product 102 and one or more magnets affixed to the measuring device 104; alternately, the metallic strip may be affixed to the measuring device 104 and one or more magnets may be affixed to the measuring device 104. In another example, the fastening attachment mechanism may include a fastener that includes a first strip (e.g. first fabric strip) with tiny hooks that can mate with a second strip (e.g. second fabric strip) with smaller loops such that the hooks temporarily mate with the loops until they are pulled apart; in such case, the first strip can be affixed to the product 102 while the second strip can be affixed to the measuring device 104, or the second strip can be affixed to the product 102 while the first strip can be affixed to the measuring device 104. For the attachment mechanism of taping, different types of tapes can be used for coupling the product 102 and the measuring device 104, depending on how strong or long the attachment is desired. For example, materials and/or thickness forming the tape can vary based on attachment strength and/or length, and different examples of such materials include polypropylene, polyurethane, thermoplastic olefin, low-surface-energy clear coat systems, rubber (e.g. EPDM rubber), and/or the like.

In some implementations, the product 102 can be communicatively coupled to the measuring device 104 over one or more communication networks, as noted above. For example, a measuring device 104 can detect motion of the product 104, or any component or substance within the product, from a distance (i.e. the detection may be performed remotely, without any attachment or wired connection between the product and the motion sensor). The motion sensors can be infrared-based motion sensors, optics-based motion sensors, radio-frequency-based motion sensors, sound-based motion sensors, vibration-based motion sensors, and/or magnetism-based motion sensors. The infrared-based motion sensors can include passive sensors and/or active sensors. The optics-based motion sensors can include video and/or camera systems. The radio-frequency-based motion sensors can include sensors based on radar, microwave and/or tomographic signals. The sound-based motion sensors can include microphones and/or acoustic sensors. The vibration-based motion sensors can include triboelectric, seismic, and/or inertia-switch sensors. The magnetism-based motion sensors can include magnetic sensors and/or magnetometers.

Example Electronics for the Measuring Device

The measuring device 104 includes one or more sensors to measure various features or characteristics of the product. For example, the one more sensors may include a weight sensor to determine a weight of the product 102, a motion sensor to determine a motion of the product 102, and time sensor to determine time-duration of consumption or usage of the product 102. Some additional or alternate examples of sensors can be those configured to detect other features or characteristics including form of the product 102 (e.g. solid, liquid, or gas), shape of the product 102, volume of the product 102, cohesive properties of the product 102, adhesive properties of the product 102, surface tension of the product 102, capillary action of the product 102, pressure of the product 102, temperature of the product 102 when the product is to be used and/or stored, viscosity of the product 102, and/or the like.

The measuring device 104 further includes a communication module, which can include communication circuitry, to enable communication between the measuring device 104 and other components of the system 100, such as the communication device 106 and the computing device 110. The term module, as noted herein, can include software instructions and codes to perform a designated task or a function. A module as used herein can be a software module or a hardware module. A software module can be a part of a computer program, which can include multiple independently developed modules that can be combined or linked via a linking module. A software module can include one or more software routines. A software routine is computer readable code that performs a corresponding procedure or function. A hardware module can be a self-contained component with an independent circuitry that can perform various operations described herein.

The measuring device 104 can include an electronic switch that can activate and/or deactivate the measuring of the characteristics (e.g. weight, motion, location, and/or the like) of the product 102 by the measuring device 104. In some implementations, the activation or deactivation of the electronic switch can be controlled remotely by the communication device 106 and/or the computing device 108. In some implementations, the electronic switch may be in an activated position, and the manufacturer of the measuring device 104 may position the electronic switch inside the measuring device 104 such that the electronic switch cannot be deactivated without expert knowledge of opening and repairing such measuring devices. In other implementations, the electronic switch may be positioned on an exterior (e.g. housing) of the measuring device 104 such that any user may operate the electronic switch so as to activate or deactivate the electronic switch. The electronic switch, when activated, can commence measurement by the one or more sensors of the measuring device 104. The electronic switch, when deactivated, can pause or stop measurement by the one or more sensors of the measuring device 104.

In some implementations, the measuring device 104 may have minimal electronic circuitry, such as one or more sensors and a transmitter that transmit all of the detected data in real-time or at programmed (or programmable) intervals of time (e.g. every 5 seconds, every 15 seconds, every 1 minute, every 5 minutes, every 15 minutes, or any other time interval) to the computing device 108. Such implementations can advantageously make the measuring device 104 easy to use, install, and/or repair, as well as less bulky due to less weight because of less electronic circuitry within it. In such implementations, the collected data is transmitted as is from the measuring device 104 to the communication device 106 and/or the computing device 108, which devices 106 and 108 may process the collected data.

In some other implementations, the measuring device may have at least one programmable processor, and a machine-readable medium that can store instructions that, when executed by the at least one programmable processor, cause the at least one programmable processor to process the measurements by the one or more sensors before the measurements are transmitted to the computing device 108. Such implementations may be slightly bulkier due to more electronic circuitry, but such difference can be minimal. The processing by the measuring device 104 can include removal of redundancies from the collected data, and then organizing the data from which redundancies have been removed so that the organized data reduces the time taken by the communication device 106 and/or the computing device 108 to retrieve data from the measuring device 104.

In some examples, the processing to remove redundancies can include removing, from the collected data, one or more of the following: duplicative data, inconsistent data, null values, data values collected when an error was reporting during the measuring process, and/or any other erroneous values. In a few examples, the processing to remove redundancies can include normalizing the collected data to organize the data according to attributes of the collected data, and relations between different collected data. The processing can also including verifying, before transmission of the collected data, that the data to be transmitted is complete. Such processing of data can advantageously optimize the bandwidth of transmission because irrelevant or redundant data is prevented from being transmitted over the communication network 114 to the communication device 106 or computing device 108, thereby streamlining the transmission of the data over the communication network 114.

In a few implementations, the measuring device 104 may have electronic components, such as one or more controllers, one or more memories, one or more storage devices, one or more input or output devices, and/or the like. Further, while the measuring device 104 and communication device 106 are shown as separate devices, in some implementations, measuring device 104 and communication device 106 may be attached to each other. In a few implementations, the measuring device 104 and communication device 106 may be integrated with each other such that they form a single structure with a common housing and a shared set of electronic components.

Various sensors are described as being embedded within the measuring device 104. In some other implementations, at least some of those sensors can be embedded within a packaging of the product 102 while the remaining sensors can be embedded within the measuring device 104. In yet other implementations, the sensors used can be distributed across the packaging of the product 102, the measuring device 104, and the communication device 106. The communication device 106 and/or the computing device 108 can sync the sensed data between the different devices on which sensors are implemented.

Ensuring Accuracy of Collected Data

The one or more sensors on the measuring device 104 make a variety of detections or measurements. To ensure accuracy of the measurements, it needs to be ensured that the measuring device 104 is stable enough to make measurements. For example, if weight of the product 104 is to be detected, the measuring device 104 must be placed on a stable surface so as to ensure an accurate measurement of weight.

To ensure stability, the measuring device 104 can compare measurements at different time points—e.g. a first reading at 12 pm on a particular data, a second reading at 1 pm on that particular day, and a third reading at 2 pm on that particular day. If the comparison results in inconsistent data—e.g. the reading at 12 pm indicates that the product 102 weighs 4 kilograms, the reading at 1 pm indicates that the product weighs 3.8 kilograms (indicating that some of the product has been consumed), and the reading at 2 pm indicates that the product weighs 4.5 kilograms (indicating that the weight of the product 102 increased) while the product has not been refilled—the measuring device 104 can conclude (i.e. determine) that the measuring device 104 is not stable. In such case where instability has been detected, the measuring device 104 can (a) discard (or initiate a process to discard) the collected data, and/or (b) flag such inconsistency to the communication device 106 and/or the computing device 108 to notify the user to place the measuring device 104 on a stable surface. In implementations where the collected data is discarded, such discarding of data prevents improperly collected data from being used to generate insights, thereby rending the insights to be more accurate and trustworthy.

Similarly, the communication device 106 and/or the computing device 108 can also compare the data received at different times or from different devices to determine if there is any inconsistency. If the communication device 106 and/or the computing device 108 determine any inconsistency, the communication device 106 and/or the computing device 108 can discard (or initiate a process to discard) the inconsistent data and/or provide a notification to the user about the inconsistency (e.g. notification indicating that the user has mistakenly placed a different product on the measuring device 104). The process can remove any inconsistencies, including those that possibly may have originated during the transmission from the measuring device 104 to the communication device 106 and/or the computing device 108.

Example Timing of Measurements by the Measuring Device

The measuring device 104 can use an array of sensors to monitor the consumption or usage of the product 102. In some implementations, the measuring device 104 can continuously monitor the usage of the product 102 in real-time. In certain implementations, the measuring device 104 can monitor the usage of the product 102 at programmed (or programmable) intervals of time (e.g. every 1 second, every 5 seconds, every 15 seconds, every 30 seconds, every 1 minute, every 5 minutes, every 30 minutes, every 1 hour, every day, every 15 days, every 1 month, or any other time value that can be programmed). In certain implementations, the measuring device 104 can monitor the usage of the product 102 on every event by identifying actions that indicate a change. Some examples of such actions include removal of the product 108, or a portion of the product 102, to be used, refilling or placing back a product 102 for storage and/or future use, moving of the product 102, or the like.

The frequency of monitoring can vary based on (a) the storage capacity of the measuring device 104, the communication device 106, and/or the computing device 108, and/or (b) the processing capacity of the measuring device 104, the communication device 106, and/or the computing device 108, and/or (c) bandwidth of one or more channels (e.g. one or more communication channels within the communication network 108) over which the measuring device 104, the communication device 106, and/or the computing device 108 communicate with each other.

Example Structural Design of Measuring Device

The measuring device 104 can have a structure that matches the design of the product 102 to which it is coupled. For instance, where the measuring device is configured to be placed underneath the product 102, the measuring device 104 can have a cylindrical shape or a box shape (each of which can look like a coaster), which can fit underneath the product 102. If the product 102 (or packaging or housing thereof) has a particular-shaped (e.g. round, square, rectangular, polygonal, or the like) cross-section at the bottom, the measuring device 104 may have a same or similar cross-section at the top so that the combination of the measuring device 104 and the product 102 occupy the lease space for design efficiency.

In some implementations, the shape of the measuring device 104 can be customized for each product 102. In other implementations, the shape of the measuring device 104 may be based on a set of products. For example, a box-shaped measuring device 104 may be designed to be used for all products 102 that are packaged in box-shaped packaging, and a cylindrical measuring device 104 may be designed to be used for all products 102 that are often packaged in cylindrical packaging (e.g. bottles or jars), so that the mating cross-sections are similar in shape. In cases where a customized design is used for the measuring device 104, the customization may be performed to ensure (a) a compact design of the measuring device 104 or a combination of the product 102 and the measuring device 104, (b) less or optimal usage of physical space, (c) improved or optimal performance of electronic components within the measuring device 104, and/or the like.

Another Example Design of Measuring Device—Modular Design of Sensor Capsule

In some implementations, the measuring device 102 can be in the form of a physical module (which can also be referred to as a sensor capsule in some implementations, as it includes the sensors) such that the same sensor capsule can be inserted into different items such as a coaster, a tray, a sleeve (which can be configured to encompass sides of a container such as a glass or a bottle), a container, or any other accessory. The sleeve can be made of fabric, foam, plastic, or other materials. In some implementations, such items may have some means that may allow the sensor capsule to be either inserted into the item or attached to the item.

The sensor module can have a housing that can be made of plastic, rubber, and/or glass. A module as noted herein can include software instructions and codes to perform a designated task or a function. A module as used herein can be a software module or a hardware module. A software module can be a part of a computer program, which can include multiple independently developed modules that can be combined or linked via a linking module. A software module can include one or more software routines. A software routine is computer readable code that performs a corresponding procedure or function. A hardware module can be a self-contained component with an independent circuitry that can perform various operations described herein.

For the sensor capsule to be inserted into such item (e.g. coaster, tray, sleeve, container, or the like), the item may have an opening that may be designed to hold the sensor capsule. For example, a coaster may have, on top of or beneath its upper surface, a space to hold the sensor capsule. Similarly, the tray may also have, beneath its upper surface, a space to hold the sensor capsule. The sleeve may have a space at the bottom of the cylindrical sleeve so that the sensor capsule can be inserted in there. The container (e.g. cup, glass, or jug) may have a physical space at the bottom that allows the sensor capsule to be inserted in there.

For the sensor capsule to be attached to the item (e.g. coaster, tray, sleeve, container, or the like), the attachment can be performed by attachment mechanism such as gluing, knitting or threading, welding, taping, coupling using one or more of screws or nails, twisting and fitting two or more components until firmly attached (e.g. locked), pressing one component over another until firmly attached to each other (e.g. locked with respect to each other), and/or any other one or more attachment mechanisms. The attachment can be to any suitable area on the item. The area, portion or location on the item to which the sensor capsule is coupled can vary depending on the (a) features (e.g. properties or characteristics) of the product 102 that the item is designed for, and (b) the types of sensors within the sensor capsule to be used. Such features of the product 102 can include form of the product 102 (e.g. solid, liquid, or gas), shape of the product 102, volume of the product 102, cohesive properties of the product 102, adhesive properties of the product 102, surface tension of the product 102, capillary action of the product 102, pressure of the product 102, temperature of the product 102 when the product is to be used and/or stored, viscosity of the product 102, and/or the like.

For example, in some implementations, the features may require that the product 102 should be as close as possible to the sensors so that the sensor capsule can make accurate measurements, and in such case the location of coupling on the item may be chosen accordingly. In other implementations, the features may require that the product 102 should be as far as possible from the sensors so that features do not interfere with the measuring functionality or related components within the sensor capsule, and in such case the location of coupling on the item may be chosen accordingly.

In cases where the attachment requires combining of two or more separate components, any of the sensor capsule and the item may include some or all of those components, in respective implementations. For example, the magnetic attachment may involve a metallic strip affixed to the sensor capsule and one or more magnets affixed to the item; alternately, the metallic strip may be affixed to the item and one or more magnets may be affixed to the sensor capsule. In another example, the fastening attachment mechanism may include a fastener that includes a first strip (e.g. first fabric strip) with tiny hooks that can mate with a second strip (e.g. second fabric strip) with smaller loops such that the hooks temporarily mate with the loops until they are pulled apart; in such case, the first strip can be affixed to the item while the second strip can be affixed to the sensor capsule, or the second strip can be affixed to the item while the first strip can be affixed to the sensor capsule. For the attachment mechanism of taping, different types of tapes can be used for coupling the sensor capsule and the item, depending on how strong or long the attachment is desired. For example, materials and/or thickness forming the tape can vary based on attachment strength and/or length, and different examples of such materials include polypropylene, polyurethane, thermoplastic olefin, low-surface-energy clear coat systems, rubber (e.g. EPDM rubber), and/or the like.

Material forming the Measuring Device

The measuring device 104, or a housing (e.g. enclosure) of the measuring device 104, can be made of a material that is compatible with the material of the product 102 to ensure that the product 102 and/or the measuring device 104 are not harmed. For example, the measuring device 104 (or a housing of the measuring device 104) can be made of a material that can remain stable and fully operational at a temperature of storage or operation of the product 102. In some examples, the measuring device 104 (or a housing of the measuring device 104) may be configured to remain stable and fully operational in a wide temperature range, which in some examples can range from −40° C. to 150° C., in certain examples can range from 0° C. to 100° C., in few examples can range from 0° C. to 50° C. Some examples of such materials include fiberglass (which also advantageously does not absorb liquids such as water that may be present in the product 102), mineral wool (which also advantageously does not melt or support combustion, thereby making it safe to use for a variety of types of product 102), cellulose (which is also eco-friendly as it has a high amount of recycled content), polyurethane foam (which also advantageously is a sound insulator, which can be beneficial for use with loud products), and/or the like.

The measuring device 104 can have protection mechanisms to avoid being harmed from spill or leakage of the product. For example, in some implementations, the measuring device 104 can have a liquid proof or liquid resistance (e.g. water proof or water resistant) housing, which can be advantageous where the product is a liquid as the measuring device 104 may not be damaged by spill or leakage of the product 102 onto the measuring device 104. The liquid proof or liquid resistant housing can be made with liquid proof or liquid resistance materials, such as polyurethane laminate (PUL), thermoplastic polyurethane (TPU), waxed cotton, nylon, polyester, PVC-coated polyester, laminated fabric, enameled cloth, polyester fleece, microfiber, wool, vinyl, pleather, and plastic.

The measuring device 104 can additionally or alternately be made of materials that have a low coefficient of friction and are abrasion resistance, such as polytetrafluoroethylene (PTFE). Such materials can prevent or reduce friction and abrasions, and thus advantageously elongate the life of the measuring device 104.

In some implementations, the material forming the measuring device 104 may have a high strength, and some examples of such materials include dense materials such as wood or polymers, and tough materials such as steel. In a few examples, the material forming the measuring device 104 may have a high electrical resistivity, and examples of such materials include thermal insulators such as polymers and ceramics. In certain examples, the material forming the measuring device 104 may be flexible or elastic, and some examples of such materials include rubber, thermosets, or rubber. In other examples, the material may be stiff, and some examples of such materials include steel, aluminum alloy or carbon-fiber. In some examples, the material forming the measuring device 104 may be have a low cost of recycling, and some examples of such materials include metals, as they can be easily sorted, remelted and shaped. In a few examples, the material forming the measuring device 104 may have a low energy cost—which can be based on (a) energy required to collect/mine the material, and/or (b) energy required to refine, extract or synthesize the material—and an example of such material is aluminum.

Different implementations can use respective sets of one or more materials, which can be arranged in a manner that allows compactness and usage efficiency of the measuring device 104.

Activation of Measuring Device

The measuring device 104 can include an electronic switch that can activate and/or deactivate the measuring of the characteristics (e.g. weight, motion, location, and/or the like) of the product 102 by the measuring device 104, as noted above. The location of the electronic switch within the measuring device 104 can be varied to provide the ease with which the measuring can be activated or deactivated. For example, in some implementations, the electronic switch may be on the exterior (e.g. housing or enclosure) of the measuring device 104 such that the user of the product 102 can activate or deactivate the measuring. In other implementations, the electronic switch may be only in the interior of (e.g. electrical circuitry within) the measuring device 104 such that the user of the product 102 is discouraged from (or, in some implementations, prevented from) activating or deactivating the measuring device 104. In implementations where electronic switch is in the interior of the measuring device 104, the measuring device 104 may be configured to be activated or deactivated remotely by the communication device 106 and/or the computing device 108.

In some implementations, one or more controllers or processors within the measuring device may activate the measuring process (i.e. activate the sensors within the measuring device) in response to an event. Such event can vary in different examples.

For instance, in some examples, the event can be receipt of a scan by a user of a machine-readable data representation (e.g. barcode, matrix code, QR code, and/or the like).

In certain examples, the event can be formation or activation of a communication channel connecting the measuring device 104.

In other examples, the event can be receipt of a signal from another electronic component (which may or may not be shown in FIG. 1) in the system 100 that indicates that the product 102 has been, is being, or is about to be consumed or used. For instance, a controller of the measuring device 104 can activate the sensors within the measuring device 104 in response to a sensor (e.g. motion sensor) within other one or more devices (e.g. one or more of fridges, trashcans, cabinets, sinks, washing machines, dishwashers, any other one or more places or devices where the product 102 can be placed, and/or any combination thereof)—which is communicatively coupled to the measuring device 104 over a communication network, such as the communication network 114—indicating that the product 102 has been, is being, or is about to be consumed or used.

For instance, a motion sensor within a fridge may indicate opening of a door of the fridge, which may indicate that a substance of the product 102 is about to be taken out and poured into a container of the product 102. Similarly, a motion sensor within a trashcan may indicate opening of a lid of the trashcan, which may indicate that the product 102 or a substance of the product 102 is being thrown and would not be reused. In a similar manner, motion sensors within a washing machine or washer may indicate opening of a lid, which may indicate that the product 102 (e.g. dishwashing detergent or washing liquid) is being used. Similarly, a motion sensor within a cabinet may indicate opening of a cabinet door, which may indicate that the product 102 stored in the cabinet is being used.

In cases where the communication network 114 is the internet, the components of the system 100, including such other components—e.g. smart fridge, smart trashcan, smart cabinets, smart sink or the like (not shown)—can form an internet of things, which can also be referred to as internet of products.

In a few examples, the event can be confirmation of an identity of a user that is about to consume the product. The identity of the product can be created by way of the user inputting authentication data, radio frequency identification, biometrics-based identification (which may implement facial recognition, fingerprint scanning, voice identification, eye scanning, and/or the like), identification by way of magnetic stripes being used by the user, optical character recognition of data input by the user, use of one or more smart cards by the user, voice recognition, and/or the like. The user may be required to provide input to facilitate the identification on the measuring device 104. In some implementations, the user may be required to provide input to facilitate the identification on the communication device 106 (e.g. on an application—which can be a browser or a native application—on the communication device 106). The identification process to map the user to the received input data may be performed on the measuring device 104, the communication device 106, and/or the computing device 108 in various implementations.

Associating Consumption or Usage of Product with Corresponding User, and Collecting Additional User Data to Allow for Generation of More Informative Insights Associating the consumption or use of the product with a particular user can be beneficial in cases where multiple users (e.g. different members of a family) use a same product, as such implementation allows tracking consumption or usage of the product 102 by different consumers or users. This can allow generation of insights specific to each user (instead of the entire family that may be using the same product). In other examples, the techniques may be modified to allow generation of a common set of insights for all users as a whole (e.g. all the family members) that use a particular product.

The identity of the product can be created by way of the user inputting authentication data, radio frequency identification, biometrics-based identification (which may implement iris and/or facial recognition system), identification by way of magnetic stripes being used by the user, optical character recognition of data input by the user, use of one or more smart cards by the user, voice recognition, and/or the like. The user may be required to provide input to facilitate the identification on the measuring device 104. In some implementations, the user may be required to provide input to facilitate the identification on the communication device 106 (e.g. on an application—which can be a browser or a native application—on the communication device 106). The identification process to map the user to the received input data may be performed on the measuring device 104, the communication device 106, and/or the computing device 108 in various implementations. In some implementations, the identification of the user can be performed detecting proximity between the measuring device 104 and a wearable device worn by the user (e.g. bracelet, necklace, anklet, ring, watch, or the like, each of which is configured to communicate with the measuring device 104 over a communication network) when a usage event associated with the product 104 (e.g. weight change and/or motion, as detected by the measuring device 104) occurs.

In some implementations, the authentication of a user so as to confirm the identity of a user may include a combination of one or more techniques, such as a multi-factor authentication. In certain examples, the authentication can include a certificate based authentication, biometric authentication (e.g. facial recognition, fingerprint scanning, voice identification, eye scanning), token based authentication, and/or the like.

Authorization of Activation of Measuring Device

The communication device 106 and/or the computing device 108 may need to authorize the initialization of the measuring device 104. For example, a user may be required to use the communication device 106 to upload data indicating a coupling between the product 102 and the measuring device 104 (e.g. physical proximity between the product 102 and the measuring device 104, or placement, installation or attachment of the measuring device 104 on the product 102) before the measuring device 104 is activated or initialized. The data indicating the coupling can be in the form of a photograph, video, or textual data. The video or textual data can include feedback provided by the user, where such feedback can indicate or confirm the coupling.

The computing device 108 can use natural language processing techniques to analyze the textual feedback to determine that coupling has taken place, and/or use image processing techniques to analyze the photographs or videos to determine that coupling has taken place. In some implementations, the computing device 108 may implement a machine learning model to perform such natural language processing and/or image processing. In a few implementations, the coupling information can be extracted using various algorithms, such as latent semantic analysis, probabilistic latent semantic analysis, latent dirichlet allocation, correlated topic model, any other one or more identification algorithms, and/or any combination thereof.

The machine learning models used to perform such identification may have been trained on historical coupling data—i.e. data indicating or associated with coupling between (a) the measuring device 104 or similar devices and (b) the communication device 106 or similar devices and/or the computing device 108 or similar devices. The machine learning model may have been trained previously by and/or on the computing device 108 and/or any other one or more devices, which may be coupled to the computing device 108 through a communication network and provide the machine learning model to the computing device 108. In some implementations, the computing device 108 may implement a software as a service (SaaS) that performs the training and deployment of machine learning models, where such training, deployment, and/or storage of machine learning models can be performed in a cloud computing system that is coupled to the computing device 108.

The machine learning model that is trained and deployed to identify coupling be can be a supervised model (e.g. a model that involves learning a function that maps an input to an output based on example input-output pairs) or an unsupervised model (e.g. a model used to draw inferences and find patterns from input data without references to labeled outcomes). The supervised model can be a regression model (e.g. model where output is continuous) or a classification model (e.g. model where the output is discrete).

The image processing techniques can be performed by the machine learning model, or by the computing device 108 without using a machine learning model. The image processing techniques to determine coupling can be used to determine that a user physically placed the measuring device 108 adjacent to the product 102 at an appropriate location (e.g. placed a measuring device in the form of a coaster underneath the product 102). The image processing techniques that determine that the user physically placed the measuring device 108 adjacent to the product 102 at an appropriate location can involve image classification, object recognition, object tracking, semantic segmentation, instance segmentation, pattern recognition, and/or the like.

In response to determination of the coupling, the computing device 108 can transmit a signal to the measuring device 104 that can activate or initialize the measuring device 104. Ensuring a coupling before the activation or initialization of the measuring device 104 can ensure that the measuring device 104 operates only when needed so as to save—and, in turn, optimize or improve the functionality of—computing resources, including processing, storage, and transmission capabilities.

Generation of Notifications and Activation of Sensors in Response to User Confirmation A controller of the measuring device 104 can activate the sensors within the measuring device 104 in response to a sensor (e.g. motion sensor) within other one or more devices (e.g. one or more of fridges, trashcans, cabinets, sinks, washing machines, dishwashers, any other one or more places or devices where the product 102 can be placed, and/or any combination thereof)—which is communicatively coupled to the measuring device 104 over a communication network, such as the communication network 114—an activity (e.g. opening of a fridge door, lid, cabinet door, or the like) that indicates that the product 102 has been, is being, or is about to be consumed or used.

In some implementations, the controller of the measuring device 104 may not activate the sensors within the measuring device 104 in response to detection of such activity at the other device (e.g. fridge, trashcan, cabinet, sink, washing machine, dishwasher, or the like). Instead, the controller may (a) generate a notification of the activity to the user, (b) transmit a request for confirmation that the user performed such activity, and (c) activate the sensors within the measuring device 104 in response to confirmation by the user. Activation of sensors in response to confirmation by a user can ensure that data specific to the particular user is recorded by the measuring device, and prevents recording of data that should not be associated with or mapped to the user. This can, in turn, reduce the storage requirements within the measuring device 104 or any other component within the system 100 that stores the measured data, and reduce the bandwidth required for transmitting the measured data.

Collection of User Attributes and Other Attributes

To generate more informative insights, in some implementations, the communication device 106 may collect (for purposes of transmission to the computing device 108) various other details (e.g. user attributes and/or attributes of the product 102, measuring device 104, and/or communication device 106) at some point, which can be collected on an application of the communication device 106 before the user starts using the measuring device 104 to capture the consumption or usage of the product 102 by the user.

The user attributes that are collected by the communication device 106 can include name of the user, date of birth of the user, ethnicity of the user, product preferences of the user, brand preferences of the user, shopping habits of the user, consumption or usage habits of the user, and/or residential address of the user. In a few implementations, the user attributes can further include details of a household of the user, such as the number of people that live in the household, an approximate size of a house in square feet, household income, number of pets in the household, types of pets in the household, and/or describing of current living situation.

Other attributes that are collected by the communication device 106 can include details of the product 102, details of the measuring device 104, details of the communication device 106, and/or the like. The one or more details of the product 102 may include data representation on the product 102 that is readable by a machine (e.g. barcode of the product 102, QR code of the product, or the like), the name of the product 102, a merchant (e.g. manufacturers, distributors, retailers, and/or the like) of the product 102, a photograph or video of the product 102, a weight reading of the product 102, and/or the like. In some implementations, the measuring device 104 includes an inbuilt barcode scanner to scan the barcode of the product 102.

In some implementations, the communication device 106 may retrieve such attributes automatically from an application (e.g. browser or a native application) of the communication device 106. In a few implementations, the communication device 106 may retrieve such attributes automatically from an operating system of the communication device 106. The communication device 106 may retrieve these details in an automatic manner after receiving consent from the user of the communication device so as to advantageously respect and protect privacy of the user. In some implementations, the communication device 106 may retrieve such attributes in the form of an input provided or initiated by the user.

The communication device 106 may transmit these attributes to the computing device 108, which may use these attributes as well to perform machine learning for generating insights.

Provision of Data File to Communication Device and Receipt of Feedback from User while Consumption or Usage of Product The computing device 108 can transmit a message requesting the user to activate a camera device prior to consuming or using the product 102. Such message requesting activation of the camera device can be transmitted to an application (e.g. browser or native application) of the communication device 106 and/or the measuring device 104. The application can output (e.g. display or generate an audio signal indicating) the message for the user.

The camera device can be either inbuilt within the communication device 106, or external to, and communicatively coupled to, the communication device 106. In implementations where the camera device is external to the communication device 106, the camera device can be physically coupled to the communication device 106 or remotely coupled over a communication network. In this case where the camera device is external, the camera device may be in the form of a wearable device, which a user can wear.

For example, the camera device may in the form of a neckband or a necklace, which the consumer or user can wear around a neck of the user. The neckband or necklace may be worn around a part of the circumference of the neck or the entire circumference of neck. For example, in some instances, the neckband or necklace may be in the shape of an arc (which can be semi-circular, part of a circle, part of an ellipse, or the like) that can be placed around a portion of the neck. In other instances, the neckband or necklace may have a closed shape (e.g. circle, ellipse, or the like) that can close while the user wears the neckband or necklace around a neck and can open (e.g. by disengaging two ends) when the user wishes to remove the neckband or necklace around the neck.

While a neckband of necklace is described, in other implementations, the camera device can be in the form of a brace configured to be placed around a wrist of the user. In another implementation, the camera device can be in the form of a belt configured to be placed around a waist of the user. In a few implementations, the camera device can be in the form of an anklet configured to be placed around an ankle of the user. Other variations of the camera device are possible for other body parts of the user.

The camera device may include a flash to be automatically used based on the lighting at the place of capture. In some implementations, the flash can be manually activated or deactivated.

The camera device can record the consumption or usage of the product 106 by way of audio recording and/or video recording. The audio or video recording can be made in real-time (i.e. as the consumer or user consumes or uses the product 102 in response to the instructions). In other words, the audio and/or video recording can be a record showing or indicating the consumer or user consuming or using the product.

During the recording of the audio and/or video recording, the computing device 108 can transmit a data file (which can include audio, video, and/or textual components) that can include one or more instructions for the user. The one or more instructions can include one or more instructions to place the measuring device 104 at a particular location on or adjacent to the product 102, one or more instructions to hold the product 102 in a particular manner, one or more instructions to consume or use the product 102 in a specified manner, and/or the like. The audio and/or video recording can include those instructions as well as user's response to those instructions. The response of the user to the instructions can be specific actions, such as placing the measuring device 104 at a particular location on or adjacent to the product 102, holding the product 102 in a particular manner, consuming or using the product 102 in a specified manner, and/or the like. In some implementations, the data file can include questions (which can be in audio, video, and/or textual form), and the camera device can allow the user to provide responses within the data file.

The communication device 106, which includes the camera device, can transmit the audio or video recording along with the data file, which can include responses provided by the user in response to the questions, to the computing device 108. The computing device 108 can use the audio or video recording along with the data file for machine learning to generate insights.

The stability and quality of the data file (which includes audio, video, and/or text) as transmitted from the computing device 108 to the measuring device 104 and/or the communication device 106 can be improved. Similarly, the stability and quality of the data file (which includes responses provided by the consumer or user) as well as the audio and video recording as transmitted from the measuring device 104 and/or the communication device 106 to the computing device 108 can be improved. These improvements can be performed by at least one controller of the computing device 108, the communication device 106, and/or the measuring device 104 in various implementations. Such controller can attain improvements as follows.

The controller can separate data packets within data to be transmitted. The data to be transmitted is either the data file that is transmitted from the computing device 108 to the measuring device 104 and/or the communication device 106, or the data file (which includes responses provided by the consumer or user) as well as the audio and video recording that are transmitted from the measuring device 104 and/or the communication device 106 to the computing device 108. The controller can assign the data packets to multiple channels associated the communication network 114. The separated data packets can be assigned to the plurality of channels based on a continuous assessment of latency of data transmission within one or more of the plurality of channels. The controller can transmit, over those multiple channels, the data packets with metadata indicating information regarding sequence of each packet within the video. The controller can combine the transmitted data packets from different channels of those multiple channels based on the metadata.

Generation of Reminders for User to Use Product

In some implementations, the computing device 108 may allow the application within the communication device 106 to be programmed by a user to obtain reminders to consumer or use the product at programmed (or programmable) intervals, such as 1 hour, 2 hours, 6 hours, 12 hours, 1 day, 5 days, 10 days, 15 days, 1 month, or any other time interval. This feature can be beneficial in consumption of specific products, consumption of which is critical, such as medications, any other products (including food products) that may have been recommended by a clinician, perishable products such as fruits and vegetables, and/or the like. In such cases, the computing device 108 and/or the communication device 110 can cause the generation of a reminder or an alarm through the application installed on the communication device 110.

Categorization of Products on Application on Communication Device

The application on the communication device 106 can receive data that can be used by the machine learning model to generate insights. Some such data can include various actions performed by the user on the application, timestamps for performing such actions, and/or the like. In some examples, the actions can include: specification of categories of products used by the user in the past programmed (or programmable) periods of time (e.g. products used in the past 1 month, past 6 months, past 1 year, past 2 years, and/or any other time period), receipt or purchase of products used by the user in such past programmed (or programmable) periods of time determined by user input surveys or physical and/or digital receipt scans, specification of categories of products purchased but not yet used by the user, purchases of such products, barcode scans of products in a location (e.g. home or office) of the user, specification for time-preferences for consumption or usage of each product (e.g. breakfast, lunch, dinner, or the like). In some implementations, the categories may be preprogrammed for all users, but in other implementations one or more users may be authorized to modify, add, or delete at least some of the categories. Such categorization of products may also be referred to as tagging of the products. In certain implementations, such categorization or tagging of products may also be used to determine which specific products a user has been requested or instructed to place on the measuring device 104.

Internet of Things—Interaction with Other Smart Devices to Collect Additional Event Data to be Used in Machine Learning The measuring device 102, communication device 106 and/or the computing device 108 may be connected to, and retrieve data from, other one or more devices (e.g. one or more of fridges, trashcans, cabinets, sink, washer, any other one or more places or devices where the product 102 can be placed, and/or any combination thereof) that may have sensing capabilities (e.g. by way of one or more sensors within those other devices). Such data can indicate an activity (e.g. opening of a fridge door, lid, cabinet door, or the like) that indicates that the product 102 has been, is being, or is about to be consumed or used. Such connections can be over a communication network. In cases where the communication network 114 is the internet, the components of the system 100, including such other devices—e.g. smart fridge, smart trashcan, smart cabinets, smart sink or the like (not shown)—can form an internet of things, which can also be referred to as internet of products.

A controller of the measuring device 104 can activate the sensors within the measuring device 104 in response to a sensor (e.g. motion sensor) within other one or more devices (e.g. one or more of fridges, trashcans, cabinets, sinks, washing machines, dishwashers, any other one or more places or devices where the product 102 can be placed, and/or any combination thereof)—which is communicatively coupled to the measuring device 104 over a communication network, such as the communication network 114—an activity (e.g. opening of a fridge door, lid, cabinet door, or the like) that indicates that the product 102 has been, is being, or is about to be consumed or used.

The measuring device 102 and/or communication device 106 may transmit this data collected from these other devices (e.g. one or more of fridges, trashcans, cabinets, sink, any other one or more places or devices where the product 102 can be placed, and/or any combination thereof) to the computing device 108, which may such data as well to perform machine learning for generating insights.

In some implementations, the computing device 108 may detect the activity (e.g. opening or closing of a fridge door, lid, cabinet door, or the like) without using the one or more sensors that may or may not be present on those other devices (e.g. fridge, trashcan, cabinet, sink, washer, or the like). In such cases, the computing device 108 can transmit, to the communication device 106, a message requesting the user to activate a camera device to record such activity. The camera device can record such activity, such as the opening or closing of a fridge door, lid, cabinet door, or the like. The computing device 108 can retrieve the recording, and implement one or more machine learning models to determine the occurrence of the activity. The computing device 108 can then, upon detection of the occurrence of the activity, transmit instructions to the measuring device 104 or the communication device 106 to activate or deactivate the sensors within the measuring device. These implementations can be advantageous in cases where it is difficult to place sensors within one or more of those other devices (e.g. fridge, trashcan, cabinet, sink, washer, or the like) to detect the activity (e.g. opening of a fridge door, lid, cabinet door, or the like).

Additional Features of Smart Devices

Some of the smart devices that can be a part of the system 100 include a fridge, trashcan, cabinet, sink, washer, dishwasher, and/or the like. Such devices may be referred to as a smart device because of the incorporation of electronic circuitry within them, which can include sensors, as described above.

In some implementations, the smart devices can also include cameras within them. Such camera can be used to read machine-readable data representation (e.g. barcode, matrix code, QR code, and/or the like) of a product placed within that smart device so as to identify the product, and determine (based on the type of smart device) whether the product is being stored, used, or discarded. For example, a product 102 placed in the trashcan indicates that the product is being discarded, a product 102 placed in the washer indicates that the product is being used, a product 102 placed in the cabinet indicates that the product is being stored.

The smart devices can further include weight sensors, time sensors, location sensors, energy or power meters, and any other sensor (which are separate from, but similar to, the sensors within the measuring device 104). The weight sensors can indicate the weight of the product 102 at different times, which can further indicate the consumption or usage of the product 102. The time sensors can determine the time for which the consumption or usage has been determined. The location sensors can include a global positioning system (GPS) device that indicate an address location of the smart device, and an internal location sensor that can indicate an internal location within the smart device (e.g. second tray from top within the smart fridge), and/or the like.

In some implementations, the motion of an object—which has already been located—may be used to infer the modifications in the location of that object. The motion of the object can be measured by a motion sensor, which can be one or more of infrared-based motion sensors, optics-based motion sensors, radio-frequency-based motion sensors, sound-based motion sensors, vibration-based motion sensors, and/or magnetism-based motion sensors. The infrared-based motion sensors can include passive sensors and/or active sensors. The optics-based motion sensors can include video and/or camera systems. The radio-frequency-based motion sensors can include sensors based on radar, microwave and/or tomographic signals. The sound-based motion sensors can include microphones and/or acoustic sensors. The vibration-based motion sensors can include triboelectric, seismic, and/or inertia-switch sensors. The magnetism-based motion sensors can include magnetic sensors and/or magnetometers.

The computing device 108 can receive timestamped data, including outputs of each of these sensors, from the smart devices either directly or via the communication device 106. Such data can be input to the machine learning model for a more accurate and/or detailed generation of insights.

Installation of the Smart Device

While the smart device is installed, the application (e.g. browser or native application) of the communication device 106 may provide instructions to the user for installation of the smart device. The application may require the user to input some information to complete the installation process. The computing device 108 can provide such information as input to the machine learning model that is used to generate insights. Such data can include details of a user (which can include details that can uniquely identify the user), specific features of the smart device that have been programmed by the user, preferences of the user for using the smart device, desired operations of the smart device, and/or the like.

Syncing of Product Consumption or Usage

To ensure that each component within the system 100 has the most recent data on consumption or usage of the product 102, the components within the system 100—including the measuring device 104, communication device 106, computing device 108, and the smart devices—can sync with each other. The term sync can also be referred to as synchronization, docking, cradling, and/or the like. In some implementations, the syncing may occur at programmed (or programmable) intervals of time, such as 30 seconds, 1 minute, 5 minutes, 30 minutes, 1 hour, 6 hours, 12 hours, 1 day, 2 days, 5 days, or the like. The lower the time interval, the more accurate will the insights be. Also, this implementation where syncing occurs at specific intervals conserves computing resources as compared to an implementation where syncing occurs in real-time. In certain implementations, the syncing may occur in real-time, and this implementation can advantageously result in generation of more accurate insights.

To sync all of these devices in the system 100, the computing device 108 can update a software with data received from any of these devices, and render that updated data in software to each of the devices so that each device has the most recent data at the time of syncing. The computing device 108 can communicate with each other by way of communication network 114, and/or any other one or more communication networks. Some such communication networks can include Bluetooth communication, Bluetooth Low energy, Wi-Fi, cellular networks, or any other communication network. In some implementations, the communication network connecting two or more smart devices described herein can be a low-power, low data rate, and close proximity (e.g., personal area) wireless ad hoc network such as a Zigbee network. In certain implementations, the communication networks can be any low-rate personal area network, operation of which may be defined by the technical standard IEEE 802.15.4. In few implementations, the communication network can be any network implementing a Bluetooth Mesh, which is a computer mesh networking standard based on Bluetooth Low Energy that allows for many-to-many communication over Bluetooth radio.

Computing Device, and Generation of Insights and Rewards

The computing device 108 can use the data generated within the system 100 to generate insights. Such generation of insights is now explained.

The sensors within the measuring device 104 can detect respective features. For example, the one or more weight sensors can weigh the product 102, the one or more motion sensors can detect a motion of the product 102, and one or more time sensors can observe a time consumed by the weight sensor and/or the motion sensor. The motion sensor may detect a movement of the product 102 to generate motion data. In some implementations, the sensor unit includes an accelerometer to detect the movement of the product 102 to, for example, confirm the usage of the product 102. The weight sensor may weigh the product 102 when the product 102 is placed on the stable condition after the movement and generate weigh data. The time sensor may observe the time consumed on the weight sensor and the motion sensor to generate time consumed data. The time sensor may timestamp the usage of the product 102. The time sensor can be a clock or a timer. Optionally, the timestamp includes morning, afternoon, evening and night. The timestamp may include the real-time usage of the product 102.

In some implementations, the measuring device 104 may be used for a single product 102. For example, the measuring device 104 may be disposed or discarded after consumption or usage or the product 102. In other implementations, the same measuring device 104 may be reused for several different products. For example, the measuring device 104 may be used to perform measurements for the product 102, and subsequently the consumer or user may couple the measuring device 104 to another product so as to perform measurements for the other product. In some implementations, the computing device 108 may permit the consumer or user to couple a new product with the measuring device 104 only after measurements of the product 102 have been completed or the product 102 has been fully consumed (e.g. the computing device 108 may permit scanning a barcode of the new product and capturing the photograph (or video in some implementations) of the new product on a camera of the communication device 106 only after the measurements for the product 102 have been completed). This advantageously avoids errors in measurements for different products by keeping measurements for different products discrete. While measurements for different products are taken separately, as explained above, in other implementations the computing device 108 may allow the measuring device 104 to be coupled to multiple products, whereby the measuring device 104 can include some processing capability to organize the measurements for different products separately. In such cases, the processing by the measuring device 104 prevents frequent back and forth of substantial amount of data over the communication network 114, which can reduce bandwidth usage and decrease latency.

In a few implementations, the measuring device 104 includes a space for a label that can be manually stuck on the measuring device 104, or a digital label that can be programmed from any of an application, communication device 106, computing device 108, client device 110, any other one or more computers, and/or a cloud platform.

The measuring device 104 transmits the weigh data, the motion data, the time consumed data, location data, and any other related data of the product 102 to the computing device 108 through the communication network 114. The computing device 108 also receives the data (e.g. video or audio) showing the consumption or usage of the product 102 along with the feedback from the consumer or user (which can be in the form of video, audio, or text such as responses to preset questions; which can be superimposed on the data—e.g. video or audio—showing the consumption or usage of the product 102 by the consumer or user).

Machine Learning to Generate Insights, Recommendations, and/or Rewards

The computing device 108 can input all of this data received from the measuring device 104 and the communication device 106 to a trained machine learning model to generate the insights. The machine learning model may have been trained on historical weigh data, historical motion data, historical time consumed data, and/or other similar data, all of which can be of the consumer or user and/or other consumer or users of same or similar products. The machine learning model may have been trained previously by and/or on the computing device 110 and/or any other one or more devices.

The machine learning model that is trained and deployed to perform machine learning can be a supervised model (e.g. a model that involves learning a function that maps an input to an output based on example input-output pairs) or an unsupervised model (e.g. a model used to draw inferences and find patterns from input data without references to labeled outcomes). The supervised model can be a regression model (e.g. model where output is continuous) or a classification model (e.g. model where the output is discrete).

The regression model can be one or more of: (a) a linear regression model (e.g. a model that finds a line or curve that best fits the data), (b) a decision tree model (e.g. a model that has nodes, where the last nodes of the tree that are also referred to as leaves of the tree make decisions, where the number of nodes can be increased to enhance accuracy of the decision making and number of nodes can be decreased to enhance speed to reduce latency), (c) random forest model (e.g. model that involves creating multiple decision trees using bootstrapped datasets of the original data and randomly selecting a subset of variables at each step of the decision tree, where this model advantageously reduces the risk of error from an individual tree), (d) a neural network (e.g. a model that receives a vector of inputs, performs equations at various stages, and generates a vector of outputs), and/or the like.

The classification model can be one or more of: (a) a logistic regression model (e.g. a model that is similar to linear regression but is used to model the probability of a finite number of—e.g. two—outcomes; for instance, a logistic curve or equation may be created in such a way that the output values can only be between 0 and 1), (b) a support vector machine (e.g. a model that finds a hyperplane or a boundary between two classes of data that maximizes the margin or distance between the two classes), (c) naïve bayes model (e.g. a model that determines a class by implementing the bayes theorem).

The unsupervised learning models can be one or more of: (a) clustering models (e.g. a model that involves the grouping, or clustering, of data points, wherein such models can involve various clustering techniques such as k-means clustering, hierarchical clustering, mean shift clustering, and density-based clustering), and (b) dimensionality reduction models (e.g. a model that eliminates or extracts features to reduce the number of random variables under consideration by obtaining a set of principal variables), and/or the like.

The computing device 108 can implement any of these machine learning models to generates insights based on data received from the measuring device 104 and the communication device 106. Some insights are specific to and beneficial for the consumer or user, and certain insights are specific to and beneficial for a merchant (e.g. manufacturers, distributors, retailers, and/or the like) of the product. The insights can include qualitative insights and quantitative insights.

The computing device 108 can (a) implement a rewards system to reward the consumer or user for tracking the consumption or usage of the product 102, (b) generate a report that will be helpful for an entity (e.g. merchant—such as manufacturers, distributors, retailers, and/or the like—of the product 102), and (c) generate a report that will be helpful for the consumer or user. The reports can include respective insights, which can be qualitative and/or quantitative in various implementations.

The rewards system can be a points based system to determine reward points to the consumer or user for tracking his or her consumption or usage of the product 102. In various implementations, the computing device can allocate reward points to the consumer or user based on (a) usage of one or more devices for tracking consumption or usage of one or more products, (b) using the communication device 106 for performing various activities (e.g. responding to various prompts in the form of questions, such as survey questions, or requests for performance of tasks, such as video, photo, and/or audio tasks), and/or the like. The computing device 108 can also map the rewards points to one or more payment means such as cash, gift cards, cryptocurrency, or the like.

The computing device 108 can generate one or more reports including the qualitative insights and the quantitative insights. For example, the computing device 108 can generate a report for the consumer or user that includes the insights specific to the consumer or user, and another report for the entity (e.g. merchant—such as manufacturers, distributors, retailers, and/or the like—of the product) that includes the insights specific to the entity.

The qualitative and quantitative insights may include the usage of the product 102 at various time periods. The report may include any of: a graphical representation of the usage of the product 102 over a period of time, and/or a tabular column elaborating the usage of the product 102 over the period of time. In some implementations, the period of time can vary from a first time (e.g. week 1) to a subsequent or last time (e.g. week 52). In a few implementations, the report includes the graphical representation of the consumption or usage of one or more products used by the consumer or user. In certain implementations, the report includes the graphical representation of the usage of one particular product. The computing device 108 generates report with qualitative and quantitative insights that reflect accurate usage and/or consumption of the product 102 with less or no human intervention or error. In some implementations, the computing device 108 generates report that includes the qualitative and quantitative insights comprising the usage of one or more products by one or more consumers or users and the timestamps to determine the usage behavior of the one or more products by the one or more consumers or users.

Transmission of Report with Insights and Rewards to Communication Device and Client Device The computing device 108 can transmit data characterizing the rewards earned by the user of the product 102 to the communication device 106, which can output (e.g. display) the data for the user.

The computing device 108 can transmit the report specific to the entity (e.g. merchant—such as manufacturers, distributors, retailers, and/or the like—of the product) to the client device 110. The report specific to the entity may not identify users whose consumption or usage is reported so as to ensure and protect user privacy. The report specific to the entity can however refer to different users anonymously without providing any information that can compromise confidentiality or privacy of individual users. In some implementations, the report specific to a merchant can include (a) different products, which include the product 102, specific to and associated with that merchant, (b) characteristics of each product, (c) various analytical metrics associated with each characteristic, (d) consumption of usage behavior of all users in aggregate or with a common feature (e.g. same geographic region, same bracket for income, same gender, same education level, and/or the like) for each product, and/or the like. Such report can advantageously enable the entity (e.g. merchant) to assess their product campaigns, create new products, and make modifications to existing products, content of products, manufacturing processes, advertising campaigns, distribution channels, and/or any other purpose.

The computing device 108 can transmit the report specific to the user of the product 102 to the communication device 106. The report specific to the user can indicate the consumption or usage behavior of the user for various products, including the product 102. For example, the report can specify (a) the categories of products that the user has consumed or used (e.g. convenience products, shopping products, specialty products, and/or unsought products), (b) consumption or usage of products in each category, (c) a quantity of consumption or usage of each product, and/or the like. Such report can advantageously enable the user to make an informed decision to modify consumption and/or usage behavior (e.g. habits).

Use of Data Platform (e.g. Software as a Service)

In some implementations, the computing device 108 may be integrated as with the communication device 106 and/or the client device 110 as a data platform to provide services to clients. The data platform may be integrated with the computing device 108 to provide services organized by product category, country, potentially audience type/size, and/or the like. An example of such data platform is a software as a service (SaaS) platform. In such cases, the computing device 108 can be a cloud computing server, which can provide services on demand such that the SaaS platform is also termed as an on-demand software.

In some implementations, the SaaS platform can have a multitenant architecture. In a multitenant architecture, a single version of the application facilitated by the computing device 108, with a single configuration for hardware, network, operating system is used for all consumers or users (which are also referred to as tenants within the scope of multitenant architecture). This architecture can be advantageous over traditional software, where multiple physical copies of the software—each potentially of a different version, with a potentially different configuration, and often customized—may be installed across various customer sites, because SaaS allows the underlying device on which SaaS is used (e.g. communication device 106 and/or the client device 110) to be a thin client, which can be a low-performing computer that has been optimized for establishing a remote connection with a server-based computing environment.

While a multitenant architecture is described, in other implementations the SaaS platform can implement other mechanisms such as virtualization. Virtualization can be creation of a virtual machine that acts like a real computer with an operating system. Software executed on a virtual machine can be separated from the underlying hardware resources.

While the data platform is described above as a SaaS platform, in some implementations the data platform can be an infrastructure as a service (IaaS), a platform as a service (PaaS), a desktop as a service (DaaS), managed software as a service (MSaaS), mobile backend as a service (MBaaS), datacenter as a service (DCaaS), information technology management as a service (ITMaaS), and/or the like.

Some Examples of Product

Some examples of the product 102, as described herein, include cleaning liquids, wipes, sprays, floor cleaning pads, body-wash, shampoo, hand-soap, sauce cans, beverages, alcohols and/or the like. The product 102 can be categorized as customer packaged goods (CPG), fast-moving consumer goods (FMCG), and/or food and beverages (F&B). The CPG and F&B may include categories that includes dish care (e.g. dishwashing liquid, dishwasher pods, dishwasher spray and/or dishwasher detergent), household cleaning (e.g. surface wipes & sprays, all-purpose sprays, air freshening sprays, liquid floor cleaners and/or pad based systems), laundry & fabric care (e.g. laundry liquid, detergent, pods, fabric refresher spray, fabric softener and/or dryer sheet), personal cleaning (e.g. skin care, body wash, moisturizers, hair care, shampoo/conditioner, hand soap and/or shaving gel), family care (e.g. paper towels and/or facial tissues), fragrance (e.g. perfumes and/or deodorants), feminine care, oral care (e.g. mouthwash and/or toothpaste), personal health, alcohol and/or spirits, baking products, beverages, biscuits and/or cookies, cereals, chocolates, dairy products, fruit, gum and/or candy, ice cream, meals, pasta, pet food, snacks, spices, vegetables, yogurt, and/or the like. The application on the communication device 106 may categorize the product 102 into these categories, or allow the user to perform such categorization.

Additional Details for Measuring Device

Figure 2:
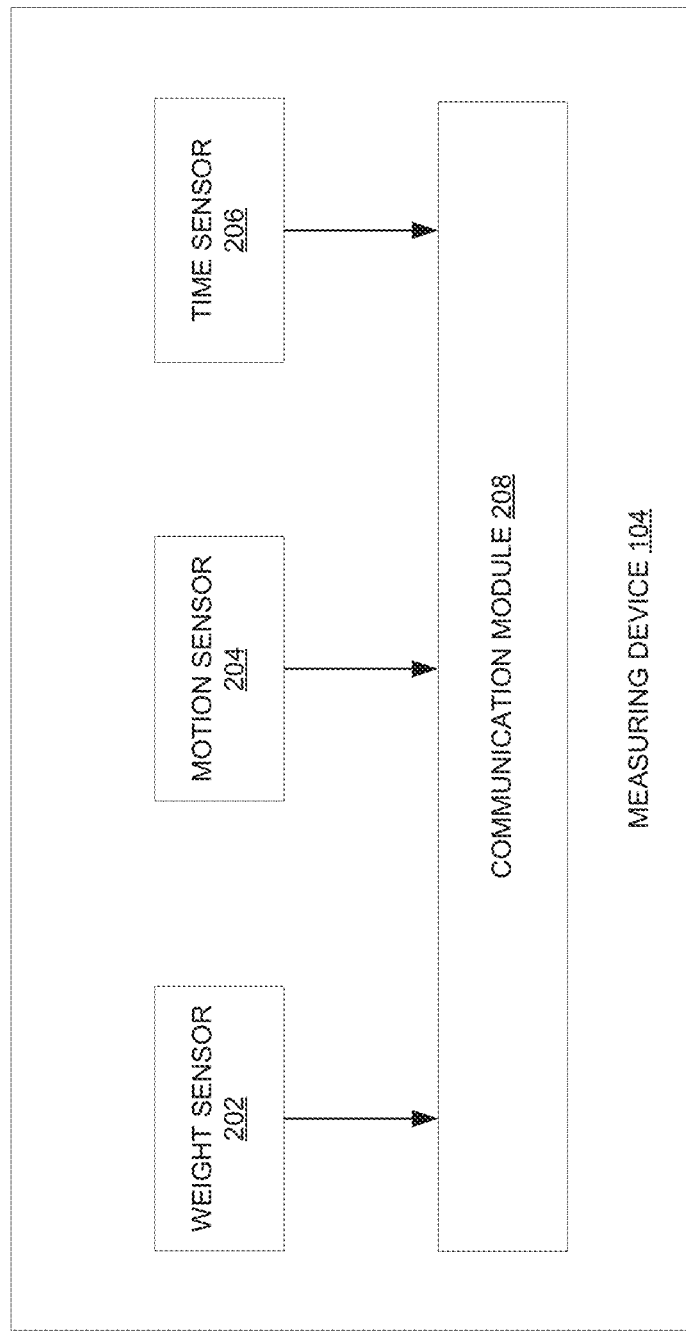
FIG. 2 illustrates an exploded view of a measuring device.

FIG. 2 illustrates one example of the measuring device 104, according to some implementations described herein. The measuring device 104 can include a weight sensor 202, a motion sensor 204, a time sensor 206 and a communication module 208. The weight sensor 202 weighs the product 102 when the product 102 is placed on the measuring device 104 and generates the weight data of the product 102. The weight sensor 202 can include at least one load cell (e.g. any number of load cells, such as four load cells), which is a transducer that converts force into a measurable electrical output that indicates weight. Any load cell described herein can be a hydraulic load cell, pneumatic load cell, strain-gauge load cell, piezoelectric load cell, inductive and reluctance load cell, magnetostrictive load cell, capacitive load cell, and/or the like. Any load cell may have any shape or size. In certain implementations, the weight sensor 202 can weigh the product 102 automatically if (a) the product 102 is in a stable condition, (b) the product 102 is used within a preset period of time (e.g. 1 hour, 2 hours, 6 hours, 12 hours, 24 hours, or any other time period), (c) the product is used regularly (e.g. at least twice, at least thrice, or so on) over a preset period of time, and/or (d) every time the product is taken away from the measuring device 104 (which may indicate usage of the product) and/or placed back on the measuring device 104. The motion sensor 204 can detect the motion of the product 102 to generate the motion data. For example, the motion sensor 204 detects the movement and/or direction of the movement of the product 102 to generate the motion data. The motion sensor 204 may be an accelerometer. The time sensor 206 detects the time consumed on the weight sensor 202 and the time consumed on the motion sensor 204 to generate the time consumed data. The time consumed data can include a time and a date. In some implementations, the time sensor 206 can timestamp one or more of the movement of the product 102, the length of time of movement of the product 102, a time when the weight sensor 202 weighs the product 102, and/or the like.

While the measuring device 104 is shown as including the weight sensor 202, motion sensor 204, and time sensor 206, in some implementations, the measuring device 104 can additionally or alternately include other sensors, such as location sensors, a temperature sensor, proximity sensor, infrared sensor, ultrasonic sensor, humidity sensor, tilt sensor, level sensor, touch sensor, and/or the like. The location sensors can include (a) a GPS sensor that can detect the geographical coordinates of the measuring device (e.g. detect a particular address such as a house or building on a map), and/or (b) an internal location sensor that can detect the particular location within a specific address (e.g. detect specific room within a house, a specific unit or apartment within a building, a shop within a shopping mall, an exhibit location within a conference, a room within a museum, and/or the like). To track the internal location using the internal location sensor, beacons can be installed in the address location (e.g. house, building, mall, or museum), and such beacons can sense proximity of the internal location sensor within the measuring device 104 from each of the beacons at either preset intervals of time or in real-time. In some implementations, there may be a one-time mapping of the beacons using the communication device 106. Using the proximity between the measuring device 104 and each of the beacons, the internal location sensor can estimate an approximate location of the measuring device 104, which can be beneficial in learning the specific internal location of the product 102 when the measuring device 104 is physically coupled (e.g. affixed or placed adjacent) to the product 102. The beacons can be Bluetooth low energy (BLE) beacons and/or IEEE 802.15.4 or low-rate wireless personal area network (LR-WPAN) beacons. In some implementations, there may not be a need for external beacons as the internal location sensors of the measuring device may work as a beacon. While beacons are described as being used to detect the internal location, in other implementations, the internal location sensor can implement other technologies to detect the internal location, such as WiFi, magnetic field detection, near field communication, gyroscope and accelerometer, ultra-wideband, and/or micro-electro-mechanical systems (MEMS) sensors, as explained below.

WiFi can be used in a similar way as BLE beacons, but this technology may require an external power source and additional equipment. In some implementations, the equipment may be expensive. In some such implementations, the BLE beacon technology may be preferred over the WiFi technology to identify an internal location of the measuring device 104. The WiFi technology can be advantageous in some implementations as compared to the BLE beacon technology because the signal in the WiFi technology can be stronger, and can cover more distance. In the magnetic field detection, the internal location sensor within the measuring device 104 can include a compass for indoor positioning, a fingerprinting technology can be used to map the magnetic fields on the venue and the measuring device 104 can use that map to find the indoor location of the measuring device 104. The magnetic field detection technology may not be implemented in certain circumstances where the magnetic fields indoor are stable. The near field communication (NFC) technology includes small chips that do not require a power source, and the internal location sensor within the measuring device 104 detects each chip to read the serial number of the chip if the measuring device 104 is within a specific distance (e.g. 30 centimeters) away from the chip. The NFC technology is advantageous in locations where the product 102 can be stored in a small space so that detections can be made within the specific distance such as 30 centimeters. A gyroscope is a device for measuring or maintaining orientation, based on the principles of conservation of angular momentum, and this orientation information can be used for even more precise positioning of the measuring device 104. Ultra-wideband (UWB) is a most precise method of detecting indoor positions. Under the UWB, UWB anchors are placed in the corners of a venue up to a preset distance (e.g. 25 meters) apart, and a UWB locator tag is attached to an asset to be tracked. The UWB locator tag can send radio signal pulses within a particular frequency range (e.g. between 3-7 GHz), which the UWB anchors can use to position the tag with some (e.g. up to 30 centimeters) accuracy in a three dimensional space and with positioning updates up to every preset time period (e.g. every 50 milliseconds).

The measuring device 104 can transmit the weigh data, the motion data, the time consumed data, and any other sensor data to the computing device 108 either directly or via the communication device 106, using the communication module 208. In certain implementations, the communication module 208 transmits the weigh data, the motion data and the time consumed data to the computing device 108 with the communication network 114. The measuring device 104 may determine the weigh data, the motion data and the time consumed data automatically when at least one of: the product 102 is in a stable condition, the product 102 is not used and/or the product 102 is used.

The term module, as noted herein, can include software instructions and codes to perform a designated task or a function. A module as used herein can be a software module or a hardware module. A software module can be a part of a computer program, which can include multiple independently developed modules that can be combined or linked via a linking module. A software module can include one or more software routines. A software routine is computer readable code that performs a corresponding procedure or function. A hardware module can be a self-contained component with an independent circuitry that can perform various operations described herein.

Communication Module within Measuring Device

Figure 3:
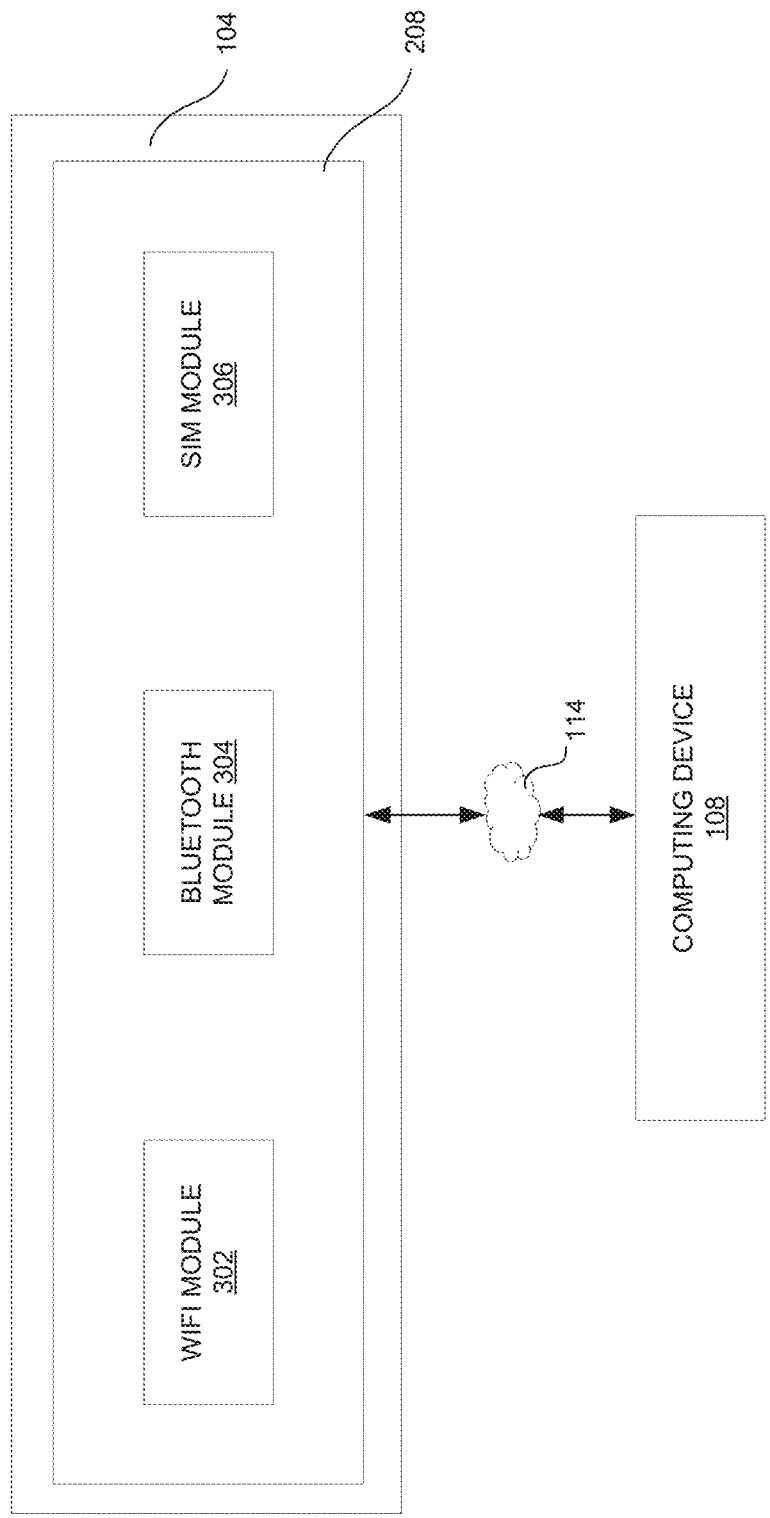
FIG. 3 illustrates an exploded view of a communication module of the measuring device that is communicatively connected to a computing device.

FIG. 3 illustrates the communication module 208 of the measuring device 104 that is communicatively connected to the computing device 108, according to some implementations described herein. The communication module 208 of the measuring device 104 is communicatively connected to the computing device 108 through the communication network 114. The communication module 208 includes at least one of a Wi-Fi module 302, a Bluetooth module 304, and/or a SIM module 306 to transmit the weigh data, the motion data and the time consumed data from the measuring device 104 to the computing device 108 through the communication network 114.

The SIM module 306 may include an IoT SIM card to provide required connectivity for transmitting the weigh data, the motion data and the time consumed data to the computing device 108 automatically. In a few implementations, the measuring device 104 transmits the weigh data, the motion data and the time consumed data to the computing device 108 automatically. In some implementations the measuring device 104 transmits the weight data, the motion data, and the time consumed data to the communication device 106 though the communication network 114, and then the data may be further transferred to the computing device 108 through the communication network 114.

While the communication module 208 is described as including a Wi-Fi module 302, a Bluetooth module 304, and a SIM module 306, in other implementations the communication module 208 may include additional or alternate modules that can enable communication over a respective communication network.

Another Example of Measuring Device

Figure 4:
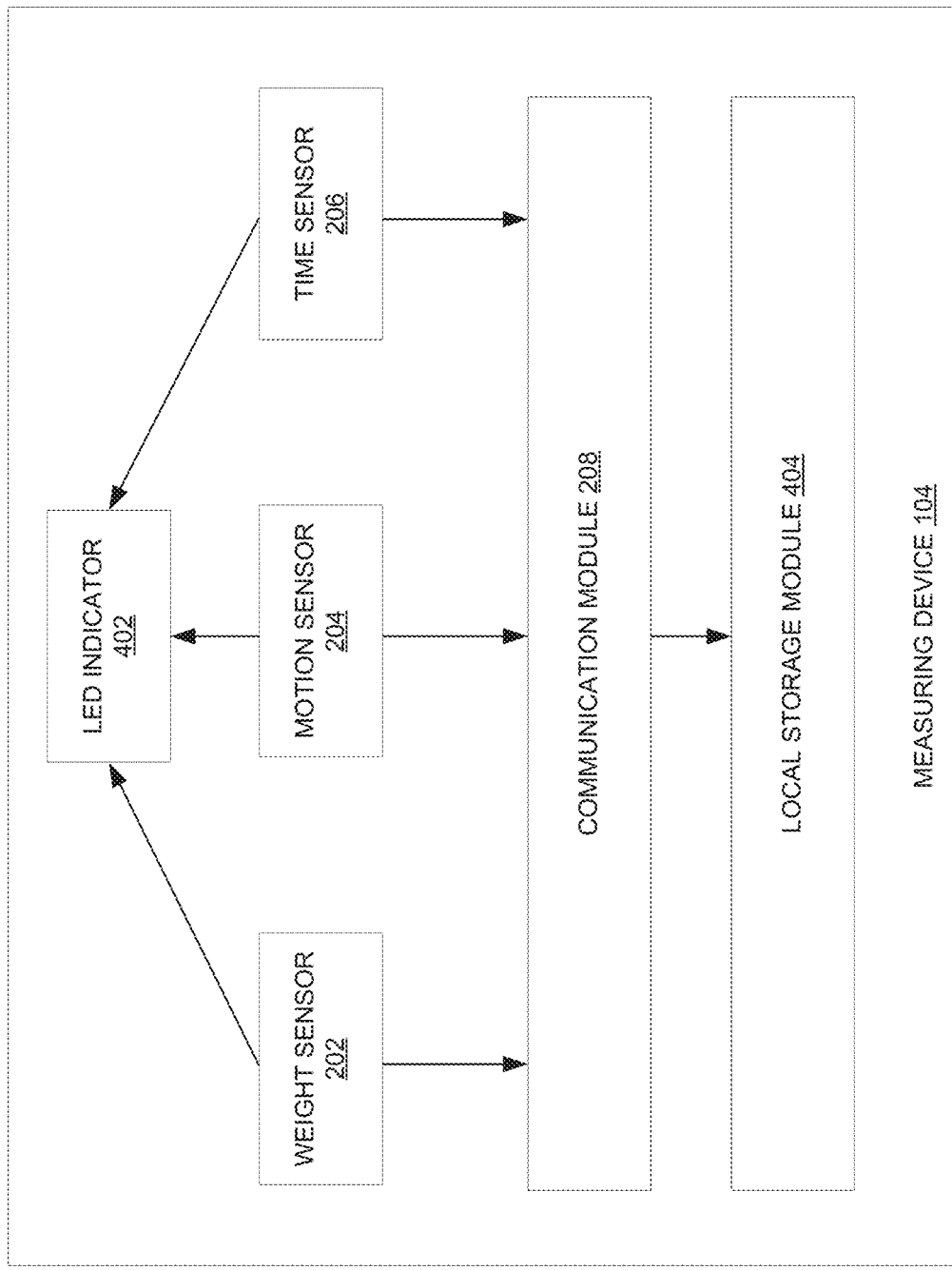
FIG. 4 illustrates an exploded view of the measuring device.

FIG. 4 illustrates another example of the measuring device 104, according to some implementations described herein. The measuring device 104 includes the weight sensor 202, the motion sensor 204, the time sensor 206, the communication module 208, an indicator (e.g. LED indicator) 402 and a local storage module 404. The LED indicator 402 indicates when the weight sensor 202, the motion sensor 204 and the time sensor 206 determines the weigh data, the motion data and the time consumed data respectively. The LED indicator 402 may indicate the weigh data to show the measurement of the product 102. Using LEDs for the indicator 402 can be beneficial for reasons such as: (a) LEDs are energy efficient, (b) LEDs require a low maintenance, (c) LEDs have a long lifespan (e.g. lifespan exceeding 10 years) because there is no filament to burn out, (d) the upfront costs of LED lighting are low, (e) LEDs emit almost no heat or ultraviolet (UV) rays, and (f) LEDs are usually not hot to touch, making them safe to handle.

While the indicator 402 is described as an LED indicator, in other implementations any other light-based indicator can be used, such as incandescent lamp, halogen lamp, fluorescent lamp, compact fluorescent lamp, high-pressure sodium lamp, and low-pressure sodium lamp. While the indicator 402 is described as a light-based indicator (i.e. indicator that emits light), in other implementations, the indicator can be an audio indicator (e.g. sound alarm) or an audio-visual indicator (e.g. alarm that can include LEDs to generate light and audio circuitry to generate sound).

The local storage module 404 can, in some implementations, store the weigh data, the motion data and the time consumed data. The local storage module 404 can be one or more of: hard disc drives (HDDs), solid state drives (SSDs), or external storage devices such as thumb drives or discs. In a particular example, the local storage module 404 can be a non-volatile memory card (e.g. SD card). Having the local storage module 404 in the architecture can be beneficial for implementations where the weigh data, the motion data and the time consumed data needs to be processed by the measuring device 104 (e.g. to organize the data, or to process the data so as to remove redundancies) before transmitting all of that data to the computing device 108 because such local storage allows a quicker access of data, which prevents upload and download of data, including redundant data, had the storage been remote from the measuring device 104. Having the local storage module 404 in the architecture can be further beneficial in some implementations where the data syncs to the computing device 108 (e.g. cloud computing server) only once or few times daily, as such local storage allows the measuring device 104 to store the data and transmit only at certain intervals, thereby preserving and optimizing bandwidth. Such local storage is also beneficial when the communication network or communication apparatus (e.g. subscriber identification module (SIM) card within the communication device 106) is temporarily inoperable or malfunctioning, as in such situations the local storage can store data until the communication apparatus is able to synchronize with the communication device 106.

The measuring device 104 may include a control key (which can also be referred to as an on/off control key) to activate (i.e. switch on) or deactivate (i.e. switch off) the measuring device 104. When the measuring device 104 is activated (i.e. switched on), the measuring device 104 may determine the weight data, the motion data and the time consumed data automatically. The measuring device 104 may be powered by a battery, and may be configured to consume low power. The battery can be primary battery (i.e. designed to be used until exhausted of energy) or rechargeable battery (i.e. can be recharged by virtue of having their chemical reactions reversed by applying electric current to the cell). In some implementations, the battery can include one or more of electrochemical cells, such as galvanic cells, electrolytic cells, fuel cells, flow cells, and/or voltaic piles. In a few implementations, the measuring device 104 may be powered by electric power extracted (e.g. received) from a power outlet.

In some implementations, the measuring device 104 automatically deactivates (i.e. switches off) when not in use, and activates (i.e. switches on) when the product 102 is used for a while, in the period of time, includes a schedule to weight the product 102 at a certain frequency and/or upon motion of the product 102. In the case of a scheduled frequency, the period of time may be any preset time, such as 1 hour, 2 hours, 4 hours, 6 hours, 12 hours, 18 hours, 24 hours, or any other value. In some implementations, only the components that may not be required (e.g. components required for WiFi or other communication) may be deactivated (e.g. powered or switched off) to save power, while other components such as the sensors (e.g. weight sensor 202, motion sensor 204, time sensor 206, and/or the like) may go into a sleep mode but can be instantly activated upon sensing a particular (e.g. respective threshold-based) change in weight, motion, or time.

Generation of Notifications to be Displayed on Communication Device

Figure 5:
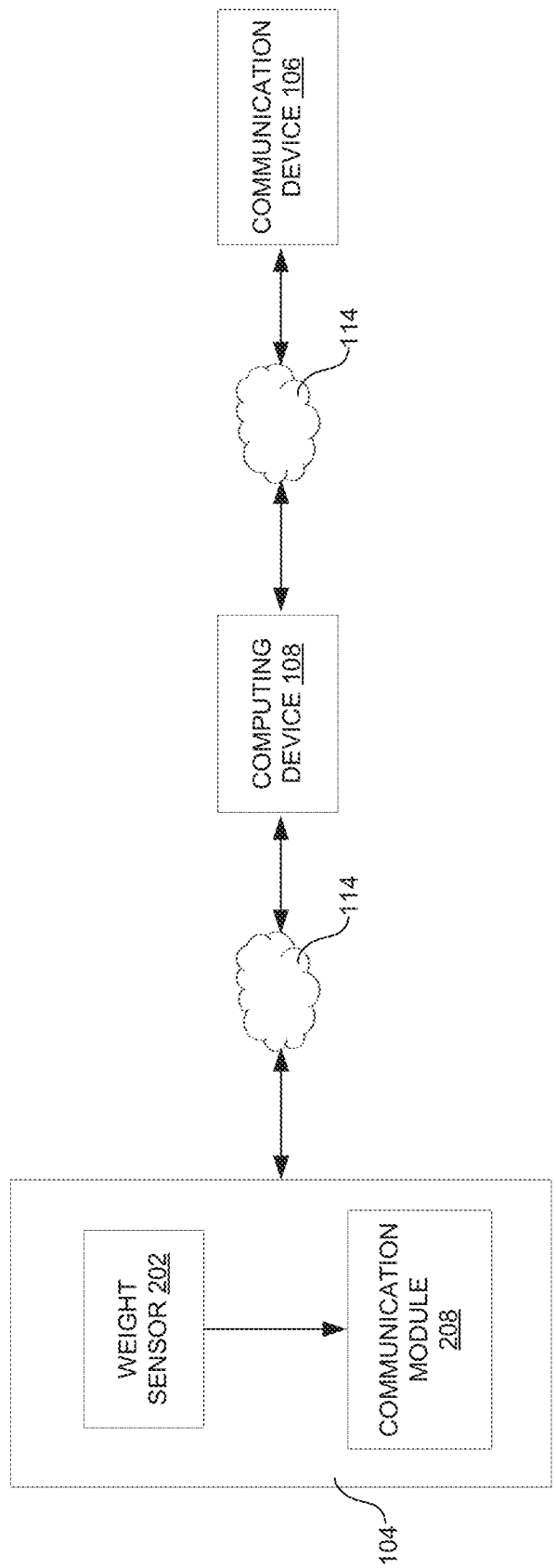
FIG. 5 illustrates an exemplary view of the measuring device that is communicatively connected to the computing device to trigger a notification on a communication device.

FIG. 5 illustrates an exemplary view of the measuring device 104 that is communicatively connected to the computing device 108 to trigger a notification on the communication device 106, according to some implementations described herein. The measuring device 104 can transmit the weigh data, the motion data and the time consumed data to the computing device 108 continuously and/or automatically. When the product 102 is finished, the weight sensor 202 may transmit zero-reading data to the computing device 108. The computing device 108 receives the zero-reading data and triggers a notification in the mobile application of the communication device 106 to check whether the product 102 is out of stock. The notification may enable the consumer or user to attach the new product to the measuring device 104. In some implementations, the notification is triggered continuously until the weight sensor 202 determines weigh data. For example, if the consumer or user forgets to change the product 102, the computing device 108 triggers a notification to attach the new product with the measuring device 104.

When the new product is attached to the measuring device 104 without scanning a barcode of the new product, the significant change in the weight may enable the computing device 108 to trigger a notification to confirm the measuring device 104 has been installed on the new product. When the measuring device 104 is not attached with any products, the computing device 108 may trigger a notification to remind the consumer or user to attach the measuring device 104 with the new product.

The consumer or user may set preferences in the mobile application of the communication device 106 to any of: receive a notification mentioning the product 102 is low and/or automatically re-order/purchase the product or add the product in a shopping list. The mobile application of the communication device 106 may be used as a home management system. The computing device 108 (and/or, in some implementations, the communication device 106) may provide additional value in the form of discounts/deals on new and/or available products and also provide recommendations on new and/or alternate products. In some implementations, the recommendations can include any of: paid advertisements or promotions and/or tailored recommendations based on overall product preferences of a consumer or user and/or all products being tracked or measured by a user and/or behavior of consumption or usage of the product 102 by the consumer or user and/or all other consumers or users of the product 102 and/or other consumers or users that are similar to the consumer or user. The recommendations can be based on actual consumption or usage behavior, and therefore are unbiased as compared to reviews that can be subjective. In some implementations, such content (e.g. advertisements, promotions, or deals) can be delivered at a time when there is only a certain threshold (e.g. percentage) of product 102 remaining (i.e. rest of the product 102 has been consumed or used). In addition to advertisements or promotions, there may be product placement sponsored by merchants to see how consumption or usage behavior of the user changes if a new product is introduced in their environment (e.g. household or business) where their measuring devices 104 are placed.

Attachment Mechanism for Connecting Measuring Device with Product

Figure 6:
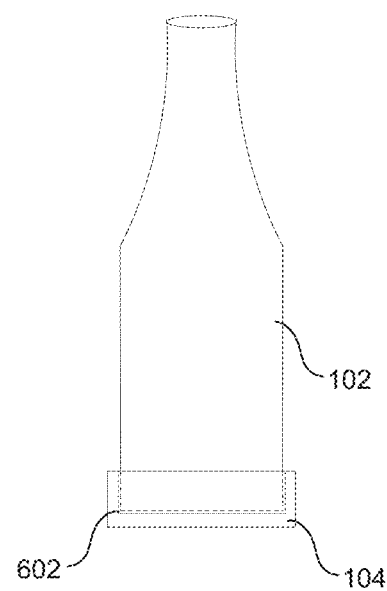
FIG. 6 illustrates an exemplary view of the product connected with the measuring device.

FIG. 6 illustrates the product 102 connected with the measuring device 104, according to some implementations described herein. The measuring device 104 includes a connector 602 that can connect (e.g. attach) the measuring device 104 with the product 102. The connecter 602 may include attachment means including gluing, knitting or threading, welding, magnetic attachment, fastening, taping, coupling using one or more of screws or nails, twisting and fitting two or more components until firmly attached (e.g. locked), pressing one component over another until firmly attached to each other (e.g. locked with respect to each other), and/or any other one or more attachment mechanisms.

System for Measurements Related to Consumption or Usage of Multiple Products

Figure 7:
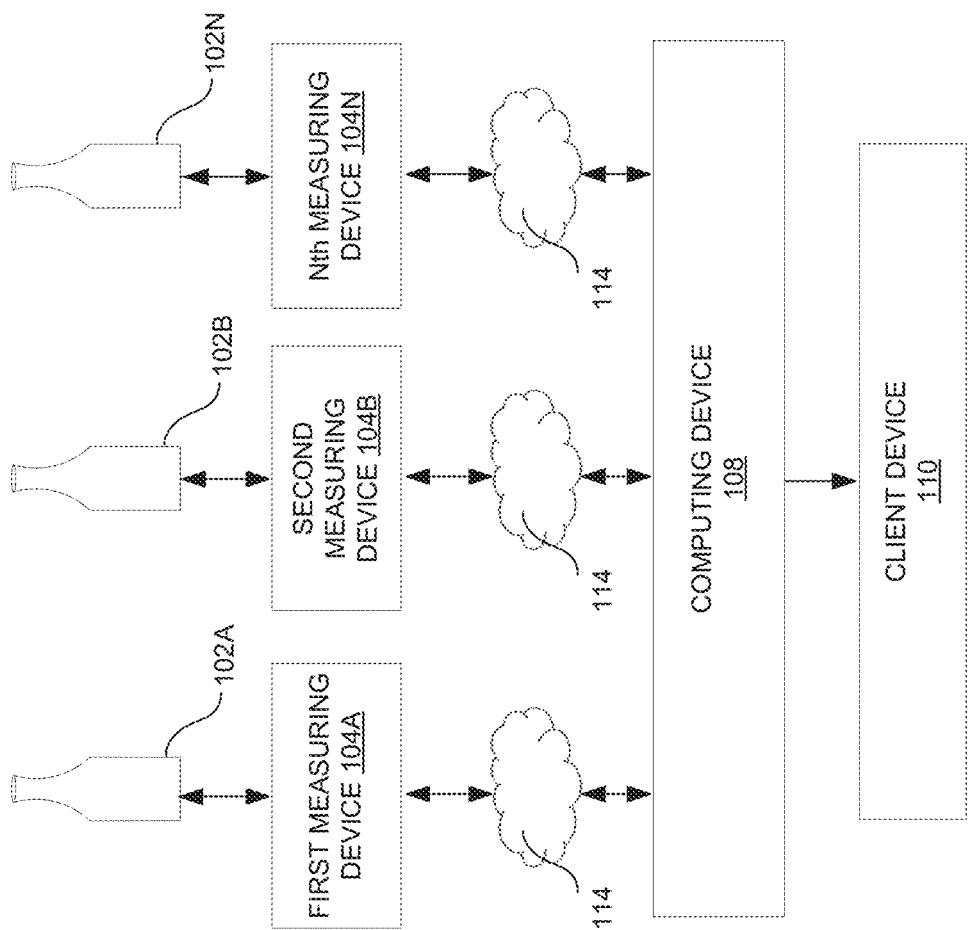
FIG. 7 illustrates an exemplary view of one or more products communicatively connected with one or more measuring devices to determine the usage behavior of the one or more products by the user.

FIG. 7 illustrates an exemplary view of one or more products 102A-N communicatively connected with one or more measuring devices 104A-N to determine the consumption or usage behavior of the one or more products 102A-N by the consumer or user, according to some implementations described herein. The one or more products 102A-N connects with the one or more measuring devices 104A-N either through one or more connectors or without any connector (e.g. the one or more products 102A-N can be connected by simply being placed on respective one or more measuring devices 104A-N). The one or more measuring devices 104A-N transmits the weigh data, the motion data and the time consumed data of the one or more products 102A-N to the computing device 108 via the communication network 114. The computing device 108 determines the consumption or usage behavior of the one or more products 102A-N by the consumer or user based on the weigh data, the motion data and the time consumed data associated with the one or more products 102A-N. The computing device 108 transmits/provides the consumption or usage behavior of the one or more products 102A-N by the consumer or user to the client device 110.

Example User Interface of Computing Device

FIG. 8 illustrates an exemplary view of a graphical user interface 800 of the computing device 108, according to some implementations described herein. The graphical user interface 800 of the computing device 108 illustrates sessions of one or more consumers or users, consumption or usage of the one or more products 102A-N by the one or more consumers or users and surveys or other activities done by the one or more consumers or users. The sessions may include a participant name of the one or more consumers or users and/or a location of the one or more consumers or users. In some implementations, the sessions include a video survey to know about the one or more consumers or users. The video survey may include questions that includes "What is your first name and where do you live?", "How often do you purchase this product?" and the like as well as tasks that include "Show us how you use this product", "Tell us your thoughts on this new concept" and the like. The video may be recorded by the communication device 106, and the communication device 106 can transmit the recorded video to the computing device 108. In some implementations, the computing device 108 transcripts the recorded video into texts. The recorded video may be filtered by any of: tasks/questions, audio keywords and/or visual objects/scenes. The recorded video may include a self-moderated interview of the one or more consumers or users who used the one or more products 102A-N.

While various specific activities are shown in FIG. 8, in some implementations there can be data for sessions of any activity to be performed by a consumer or user such as video activity, survey activity, photo activity, weigh-in activity, sensor activity, audio activity, barcode activity, receipt capture activity, screen recording activity, and/or the like. In some examples, each consumer or user may be required to perform multiple activities over a period of time.

Example User Interface of Computing Device

FIG. 9 illustrates an exemplary view of a graphical user interface 900 of the computing device 108, according to some implementations described herein. The graphical user interface 900 of the computing device 108 can include tasks/questions for initializing the product 102. The product 102 may be a dishwashing liquid. The tasks/questions may include the scanning of the product 102 using the communication device 106, weighing of the product 102 using the measuring device 104, and/or entering a reading of the measuring device 104. In certain implementations, the measuring device 104 may automatically provide the reading to the computing device 108 (either directly or through the communication device 106), and there may not be a task/ question corresponding to entering such reading of the measuring device 104 and thus the user may not be required to manually enter the reading of the measuring device 104. In some implementations, the communication device 106 scans the barcode of the product 102 and the computing device 108 determine details of the product 102 based on the barcode of the product 102. The details of the product 102 may include a barcode number, a barcode type, manufacturer, a category, a brand, an UPC detail, a base size, a sub brand, a main category, a collection, a form and/or other available barcode data. While the graphical user interface 900 is specific to a particular product (i.e. dishwashing liquid), in other implementations the graphical user interface 900 may be generated for any product (e.g. any type of product).

Example Report for User as Displayed on User Interface of Client Device

Figure 10:
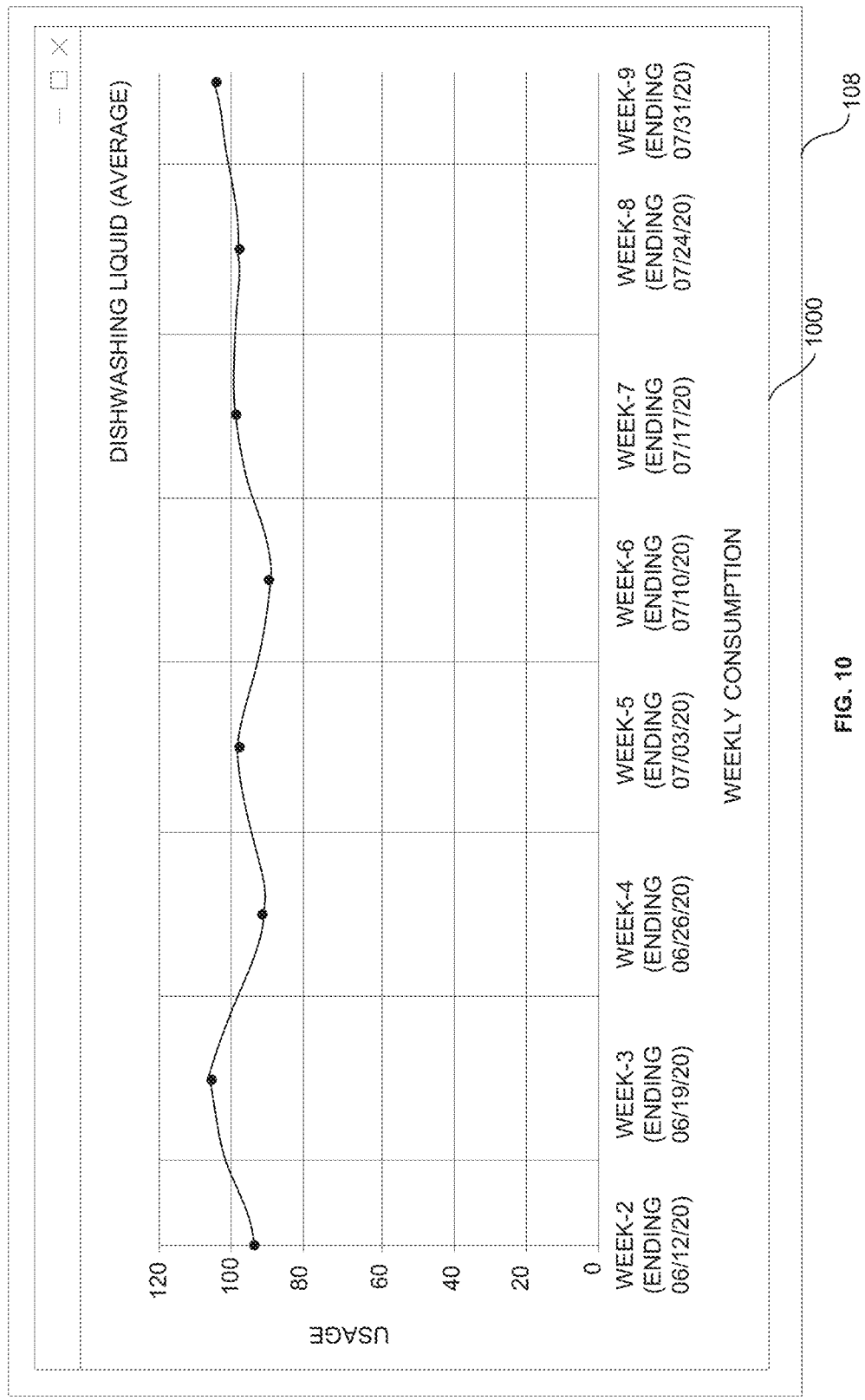
FIG. 10 is a graphical representation of a report that depicts weekly consumption of the product.

FIG. 10 is a graphical representation 1000 of a report that depicts weekly (and in some implementations, daily, hourly, particular day of any week, weekday, weekend, or any time range) consumption of the product 102, according to some implementations described herein. The graphical representation 1000 of the report includes the weekly consumption or usage of the product 102 over a period of time. The period of time may include week 1 to week 9. While the period of time is shown as 9 weeks, in some implementations the length of time can be any amount of time depending on the needs of a particular project, and/or needs and/or desire of the entity for whom insights are being generated. For example, in some variations, the length of time can be 2 weeks, 6 weeks, 12 weeks, 20 weeks, 6 months, 1 year, 2 years, 3 years, or any other length of time. The graphical representation 1000 of the report includes a Y-axis that shows the usage of the product 102 by a consumer or user and an X-axis that shows the period of time in weeks. The graphical representation 1000 includes one or more points to represent the usage of the product 102 by the consumer or user from second week to ninth week. While the graphical representation 1000 is described as being presented on the client device 110, in some implementations the graphical representation 1000 can additionally or alternately be represented on the computing device 108. Optionally, the graphical representation 1000 can be shown on the communication device 106. While the graphical representation 1000 is specific to a particular product category (i.e. dishwashing liquid), in some implementations the graphical representation 1000 may be alternately or additionally be generated for any product (e.g. dishwashing liquid by a specific brand).

Example Report for User as Displayed on Client Device

FIG. 11 is a graphical representation 1100 of a report that depicts average weekly consumption, average weekend consumption, average weekday consumption of the product 102 or the category of products that product 102 belongs to, according to some implementations described herein. While the depiction of average weekly consumption, average weekend consumption, and average weekday consumption is described, in some implementations, the techniques can be extended to monitor averages of consumption on a daily basis, hourly basis, particular day of any week, or monthly basis. The graphical representation 1100 of the report includes the average weekly consumption, average weekly consumption index week prior, the average weekend consumption, the average weekday consumption, number of weigh-ins in a same product, number of weigh-ins in a new product, number of out of stocks, and total number of weigh-ins for X number of weeks. While the graphical representation 1100 is described as being presented on the client device 110, in some implementations the graphical representation 1100 can additionally or alternately be represented on the computing device 108. Optionally, the graphical representation 1100 can be shown on the communication device 106.

While the period of time is shown as 9 weeks, in some implementations the length of time can be any amount of time depending on the needs of a particular project, and/or needs and/or desire of the entity for whom insights are being generated. For example, in some variations, the length of time can be 2 weeks, 6 weeks, 12 weeks, 20 weeks, 6 months, 1 year, 2 years, 3 years, or any other length of time.

Example User Interface as Displayed on Client Device

FIG. 12 illustrates an exemplary view of a graphical user interface 1200 of the client device 110, according to some implementations described herein. The graphical user interface 1200 includes tasks/questions for initializing any of: a second product, a third product and the like. While the graphical representation 1200 is described as being presented on the client device 110, in some implementations the graphical representation 1200 can additionally or alternately be represented on the computing device 108, or optionally on the communication device 106.

Example Report for Merchant Displayed on User Interface of Client Device

Figure 13:
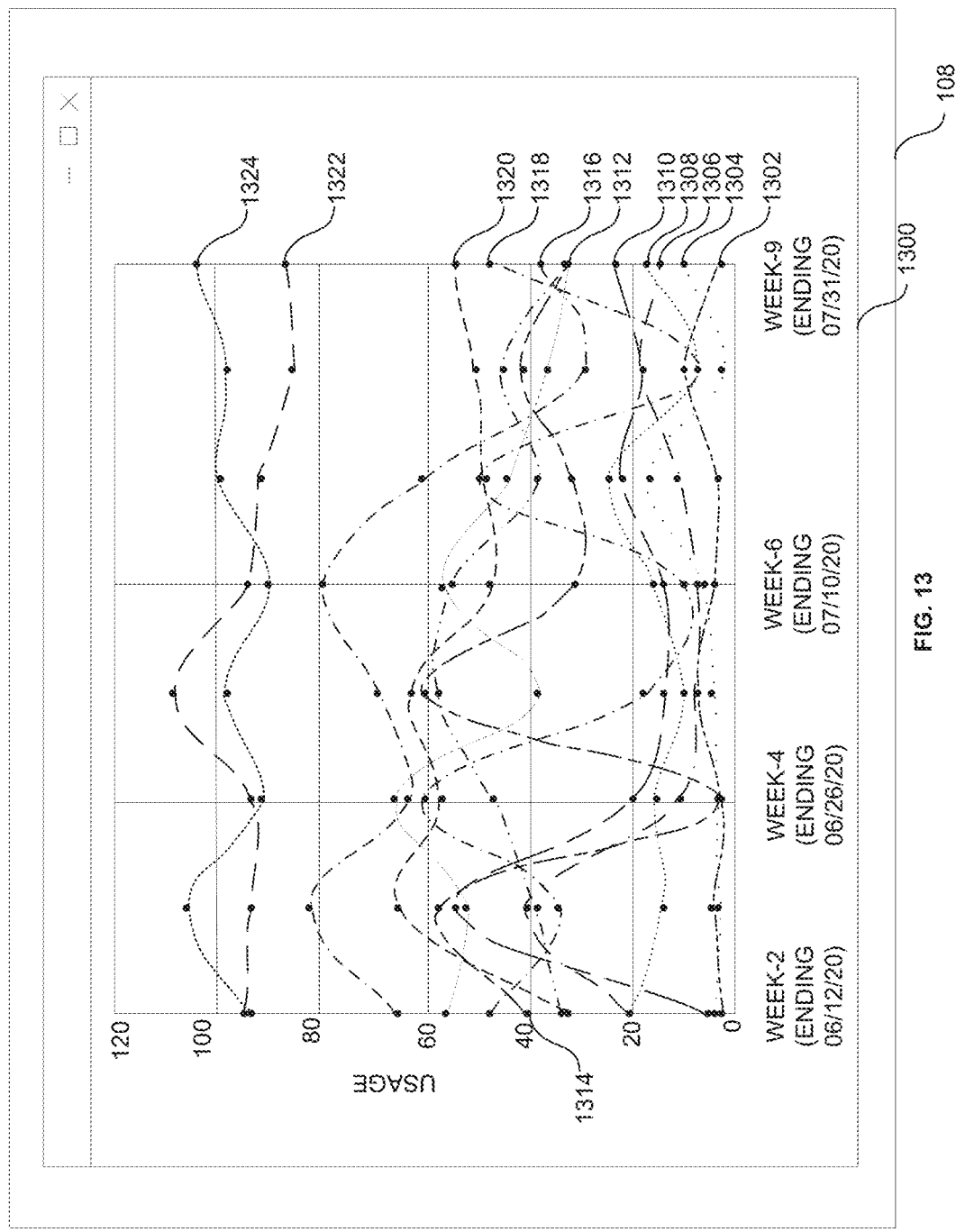
FIG. 13 is a graphical representation of a report that depicts weekly consumption details of the one or more products by the user.

FIG. 13 is a graphical representation 1300 of a report that depicts weekly (and in some implementations, daily, by time of day, day of week, or the like) consumption details of the one or more products 102A-N or categories of products by the consumer or user or groups of consumers or users, according to some implementations described herein. The graphical representation 1300 of the report includes a Y-axis that shows consumption or usage of the one or more products 102A-N and an X-axis that shows the period of time in weeks. The one or more products 102A-N includes a fabric refresher spray 1302, constant non energized air freshening products 1304, air freshening electrical plug-ins 1306, an air freshening spray 1308, cleaning system for dusting surfaces 1310, disposable dry floor cleaning wipes 1312, disposable wet floor cleaning wipes 1314, a kitchen cleaning spray 1316, sanitizing surface wipes 1318, all-purpose cleaning spray 1320, a floor cleaner 1322 and a dishwashing liquid 1324. Optionally, the graphical representation 1300 can be shown on the communication device 106.

While the period of time is shown as 9 weeks, in some implementations the length of time can be any amount of time depending on the needs of a particular project, and/or needs and/or desire of the entity for whom insights are being generated. For example, in some variations, the length of time can be 2 weeks, 6 weeks, 12 weeks, 20 weeks, 6 months, 1 year, 2 years, 3 years, or any other length of time. Further, while the graphical representation 1300 is specific to particular products as described above, in other implementations the graphical representation 1300 may be generated for any type or number of products.

Example Report for Merchant as Displayed on User Interface of Client Device

FIG. 14 is a graphical representation 1400 of a report that depicts weekly (and in some implementations, daily, by time of day, day of week, or the like) consumption of the one or more products 102A-N by the consumer or user, according to some implementations described herein. The graphical representation 1400 of the report includes the weekly consumption of the one or more products 102A-N in grams usage. While the graphical representation 1400 is specific to particular products shown in the drawing, in other implementations the graphical representation 1400 may be generated for any type or number products.

While various graphical representations are shown in FIGS. 8-14, these graphical representations are merely exemplary, and the representations can be varied or alternative representations can be generated based on data collected and tracked, needs and/or desires of entities for whom insights are generated, and/or any other one or more reasons.

Button Device for Quantifying Consumption or Usage of Product

Figure 15:
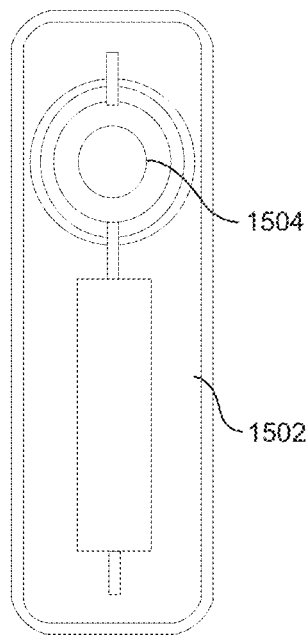
FIG. 15 is an exemplary button device to analyze the product.

FIG. 15 is an exemplary button device 1502 to analyze the product 102, according to some implementations described herein. The button device 1502 includes a button 1504 that can be pressed when the consumer or user consumes or uses the product 102. In some implementations, the button device 1502 detects the consumption or usage of the products 102 when the consumer or user manually presses the button 1504 while the consumer or user using the product 102. The button device may generate button pressing data when the consumer or user manually presses the button while the consumer or user using the product 102 and transmit the button pressing data to the computing device 108 to determine the consumption or usage behavior of the product 102 by the consumer or user. The button device 1502 may be fixed with the product 102 or the door/opening of a cabinet, fridge, or other appliances for automatic operation of the button device 1502. In an example implementation, the button device 1502 is placed inside the fridge. When the fridge is opened, the button 1504 will be activated (e.g. released) and when the fridge is closed, the button 1504 will be deactivated (e.g. pressed). In some implementations, the button device 1502 may include control configurations that includes a long press, a short press, a double press and/or a triple press and the like.

Although a button device 1502 is described for quantifying (e.g. counting) consumption or usage of the product 102, in some implementations the measuring device 104 can also or alternately perform such quantification. An example where a button device 1502 is used can be the button device 1502 determining a number of times a user has shaved in response to the user manually pressing the button each time they shave. An example where the measuring device 104 is used can be the measuring device 104 (e.g. coaster), on which shaving cream is placed, determining, using a sensor (e.g. weight sensor), amount of shaving cream that was used and in turn also determining whether the associated activity (i.e. the entire process of shaving) was completed.

Example Weighing Device to Weigh Products

Figure 16:
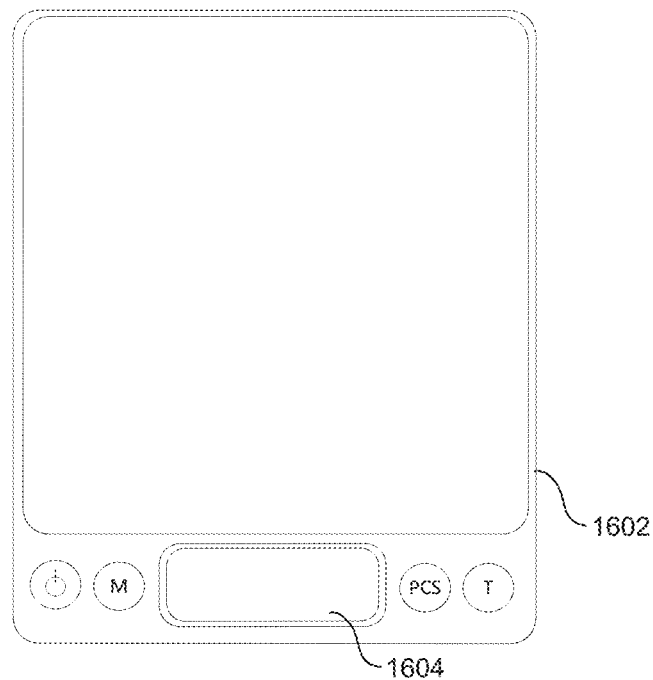
FIG. 16 is an exemplary weighing device to determine weigh data of the one or more products.

FIG. 16 is an exemplary weighing device 1602 to determine weigh data of the one or more products 102A-N, according to some implementations described herein. The one or more products 102A-N may be placed on the weighing device 1602 to determine the weigh data of the one or more products 102A-N. While the weighing device 1602 is shown as being rectangular, in another implementation the weighing device 1602 can be circular (e.g. in the form of a coaster). In yet other implementations, the weighing device 1602 can have any other shape, such as oval, polygon with any number of sides, triangular, any irregular shape, or the like. The weighing device 1602 can display the weight on an optional display 1604, which can be one or more of a liquid crystal display (LCD), electroluminescent display (ELD), light-emitting diode (LED) display, plasma display panel (PDP), quantum dot (QD) display, and/or the like. In some implementations, the weighing device 1602 may not have a display such as the display 1604.

Example Method to Generate Insights

Figure 17:
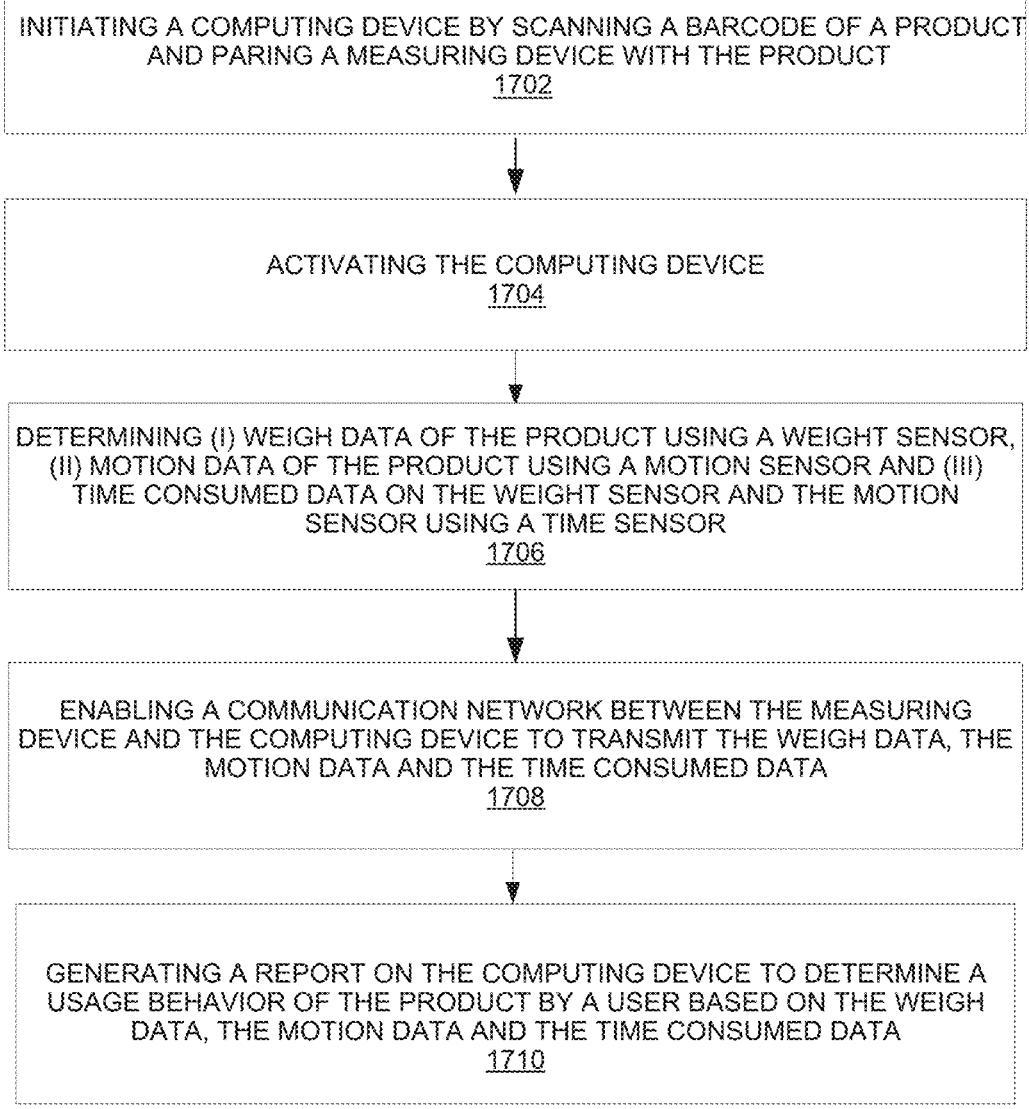
FIG. 17 is a flow diagram that illustrates a method performed by the system that generates insights on the behavior of consumption or usage of the product by the user.

FIG. 17 is a flow diagram that illustrates a method performed by the system that generates insights on the behavior of consumption or usage of the product 102 by the consumer or user, according to some implementations described herein. At step 1702, the computing device 108 can be initialized by scanning the barcode of the product 102 and paring the measuring device 104 with the product 102 using the communication device 106. At step 1704, the computing device 108 can be activated in response to paring the product 102 with the measuring device 104. At step 1706, the weigh data of the product 102 can be determined by the weight sensor 202, the motion data of the product 102 is determined by the motion sensor 204, and the time consumed data on the weight sensor 202 and the motion sensor 204 is determined by the time sensor 206. At step 1708, the communication network 114 can be enabled between the measuring device 104 and the computing device 108 to transmit the weigh data, the motion data and the time consumed data. At step 1710, a report can be generated on the computing device 108 to determine the consumption or usage behavior of the product 102 by the consumer or user based on the weigh data, the motion data and the time consumed data.

Example Measuring Device—Coaster

FIGS. 18-23 illustrate different views of an example of a measuring device 104 in the form of a coaster 1800.

FIG. 18 illustrates a top view of coaster 1800. The coaster 1800 can have female coupling portions (e.g. grooves) 1802 that can be used to combine the coaster with male coupling portions of other apparatuses, such as the sleeve shown in FIGS. 24-29 to grip (e.g. by firmly holding) the product 102 when placed on the coaster 1800. In other implementations, the coaster 1800 can include binding or constricting apparatus (e.g. clamps; not shown) to grip (e.g. by firmly holding) the product 102 when placed on the coaster 1800. Although female coupling portions 1802 are described, in some implementations, the coaster 1800 may not need to be combined with other apparatuses such as the sleeve, and thus may or may not have such female coupling portions 1802. When multiple coasters 1800 are packaged together (e.g. ten coasters packaged together), the package may contain only some sleeves (e.g. three sleeves) because a coaster 1800 would connect with a sleeve only when there is a need for the circuitry within the sleeve (e.g. when there is a need to detect location of the product 102); thus only some coasters 1800 (e.g. three or four of the ten coasters 1800 in the package) may use the female coupling portions 1802. In such package, one of the coasters 1800 can be a hub, and other coasters 1800 can be spokes, where such hub and spokes are configured to be arranged in a hub and spoke architecture (as described below, such as in FIG. 46).

FIG. 19 illustrates a side view of the coaster 1800. The coaster 1800 includes anti-slip apparatus 1804 that prevents the coaster 1800 from slipping on a surface. The anti-slip apparatus 1804 can be made of anti-slip material such as particular types of rubber, foam, polyester, fabric, and/or the like. In some examples, the anti-slip apparatus 1804 can be rubber stoppers or rubber pads. Although four anti-slip apparatus 1804 are shown in the drawings, in other implementations there can be any other number of anti-slip apparatus 1804.

FIG. 20 illustrates a bottom view of the coaster 1800. The coaster 1800 can include fastening apparatus 1806 (e.g. screws) that can combine multiple layers of the coaster 1800 or combine the coaster 1800 with other one or more apparatuses. Although screwing is described for combination, in some implementations other combination means can be used such as gluing, knitting or threading, welding, taping, coupling using one or more of screws or nails, twisting and fitting two or more components until firmly attached (e.g. locked), pressing one component over another until firmly attached to each other (e.g. locked with respect to each other), and/or any other one or more attachment mechanisms to combine materials or apparatuses. The coaster 1800 can include a power button 2002 that can be used to activate or deactivate the coaster 1800.

FIG. 21 illustrates a front view of the coaster 1800. The coaster 1800 can include a port 1808 for charging the apparatus. The coaster 1800 can include an indicator (e.g. light emitting diode indicator) 1810 that can indicate the status of charging. For example, the indicator can display a red light when the battery of the coaster 1800 is low (e.g. less than 20%), a yellow light when the battery is medium (e.g. between 20% and 70%), and a green light when the battery is high (e.g. 70% or more). In some implementations, the indicator 1810 can additionally generate a lighted notification when the coaster 1800 is being activated (i.e. turned on), deactivated (i.e. turned off), or being used. While three levels of indicators are described, in certain implementations there may be any other number of levels, each being represented by a respective color.

While a charging port of the coaster 1800 is displayed, in some implementations, the coaster 1800 may have other ports that allow the coaster 1800 to communicatively couple with some devices (e.g. computer, or peripheral devices such as mouse, keyboard, monitor or display unit, printer, speaker, flash drive, and/or the like) or the communication network. The ports can include one or more of: (a) a serial port, which can be used to couple the coaster 1800 with external modems or some computer mouse devices, (b) a parallel port, which can be used to couple the coaster 1800 with scanners or printers, (c) a PS/2 port, which can be used to couple the coaster 1800 with some computer keyboards or mouse, (d) a universal serial bus (USB) port, which can be used to couple the coaster 1800 with external USB devices such as external hard disk, printer, scanner, mouse, keyboard, or the like, (e) a video graphics array (VGA) port, which can couple a display on the coaster 1800 to a video card, (f) a power port—which can vary for different connectors, which can be a universal serial bus (USB) connector, such as a USB-A, USB-B, USB-C, micro-USB, lightning cable, and such USB can have any speed standards such as USB 1.x, 2.0, or 3.x—which can be used to receive a power cable or any other charging apparatus to charge a batter within the coaster 1800, a firewire port, which can couple the coaster 1800 to data equipment such as camcorders or video equipment, (g) a modem port, which can be used to couple the coaster 1800 with the communication network, (h) an Ethernet port, which can connect the coaster 1800 to a communication network (e.g. internet), or any other port.

FIG. 22 illustrates a top perspective view of the coaster 1800.

FIG. 23 illustrates a bottom perspective view of the coaster 1800.

Example Measuring Device—Sleeve With Coaster(s)

FIGS. 24-29 illustrate different views of an apparatus 2400 that forms the sleeve of a measuring device 104 and that is configured to be attached to a coaster 1800 to form the measuring device 104.

FIG. 24 illustrates a top view of the apparatus 2400. The apparatus 2400 includes a gripping device 2402 that is configured to move along the area 2404 to firmly grip the product 102 (as further clarified in FIG. 28).

FIG. 25 illustrates a side view of the apparatus 2400. The apparatus 2400 has male coupling portions 2502 that can couple with female coupling portions 1802 shown in FIGS. 18, 19, and 21-23.

FIG. 26 illustrates a front view of the apparatus 2400.

FIG. 27 illustrates a bottom view of the apparatus 2400. The apparatus 2400 can optionally include a quick release button 2702 that can be used to mechanically uncouple (e.g. unclamp) the product 102 from the apparatus 2400. The apparatus 2400 further includes fastening apparatus (e.g. screws) that can combine multiple layers of the apparatus 2400 and/or anti-slip apparatus that prevents the apparatus from slipping. Such fastening apparatus (e.g. screws) and additional or alternative anti-slip apparatus are collectively referenced as 2704. Although screwing is described for combination, in some implementations other combination means can be used such as gluing, knitting or threading, welding, taping, coupling using one or more of screws or nails, twisting and fitting two or more components until firmly attached (e.g. locked), pressing one component over another until firmly attached to each other (e.g. locked with respect to each other), and/or any other way to combine materials or apparatuses.

FIG. 28 illustrates a top perspective view of the apparatus 2400.

FIG. 29 illustrates a bottom perspective view of the apparatus 2400.

FIGS. 30 and 31 illustrate different views of a measuring device 104 formed by attaching the apparatus 2400 of FIGS. 24-29 with the coaster 1800 of FIGS. 18-23. The coupling is performed by coupling male coupling portions 2502 of the apparatus 2400 with female coupling portions 1802 of the coaster 1800.

Example Measuring Device—Tray with Coaster(s)

FIGS. 32-34 illustrate different views of a tray 3200 of a particular measuring device 104 that is made operable by coupling (e.g. attaching) the tray 3200 with one or more coasters 1800. The tray 3200 can be beneficial where larger or heavier items need to be weighed or measured, such as paper towels, toilet paper, diapers, pet food, or the like. While the drawings show each tray 3200 as being coupled to two coasters 1800, in some implementations, each tray 3200 may be configured to be coupled to any other number (e.g. 1, 3, 4, 5, 6, or so on) of coasters 1800. In certain implementations, the number of coasters 1800 to be coupled to a single tray 3200 may depend on the size (e.g. diameter or area) of the tray 3200 and/or the size (e.g. diameter or area) of each coaster 1800.

In some variations, a hardware component (which can also be referred to as a hardware module), which has all electrical circuitry of the coaster 1800, can be inserted into various other form factors such as a tray. In such implementations, one or more load cells (e.g. weight sensors) of the hardware module can be extended to be at the edges or corners of the tray (e.g. as opposed to being restricted within the circumference of a coaster 1800 for which the electrical circuitry may have been designed).

In some implementations, the tray 3200 can have bevels or edges at some places. In certain implementations, the tray 3200 may be flat so that the product 102 can be placed anywhere on the tray 3200.

FIGS. 35-37 illustrate different views of the measuring device 104 formed by combining the tray of FIGS. 32-34 with coasters 1800.

Example Measuring Device—Container with Coaster(s)

FIGS. 38 and 39 illustrate different views of a container 3800 of a particular measuring device 104 that is made operable by coupling (e.g. attaching) the container with a coaster 1800.

FIGS. 40-42 illustrate different views of the measuring device 104 formed, or being formed, by combining the container 3800 with a coaster 1800.

Example Adapter for Coaster

FIGS. 43-45 illustrate different views of an adapter 4300 configured to modify a form factor of the measuring device 104. The adapter 4300 can be a connector that allows for attaching various types of items to the coaster 1800, such as containers, trays, or the like. Such items can form various types, shapes, and/or sizes of measuring devices 104. Connections can be made through magnetism (e.g. adapter 4300 can have an inbuilt magnet that allows magnetic coupling), taping (e.g. using double sided tape), gluing, knitting or threading, welding, screwing, twisting and fitting two or more components until firmly attached (e.g. locked), pressing one component over another until firmly attached to each other (e.g. locked with respect to each other), and/or any other one or more attachment mechanisms.

Example Hub and Spoke Architecture for Measuring Devices

Figure 46:
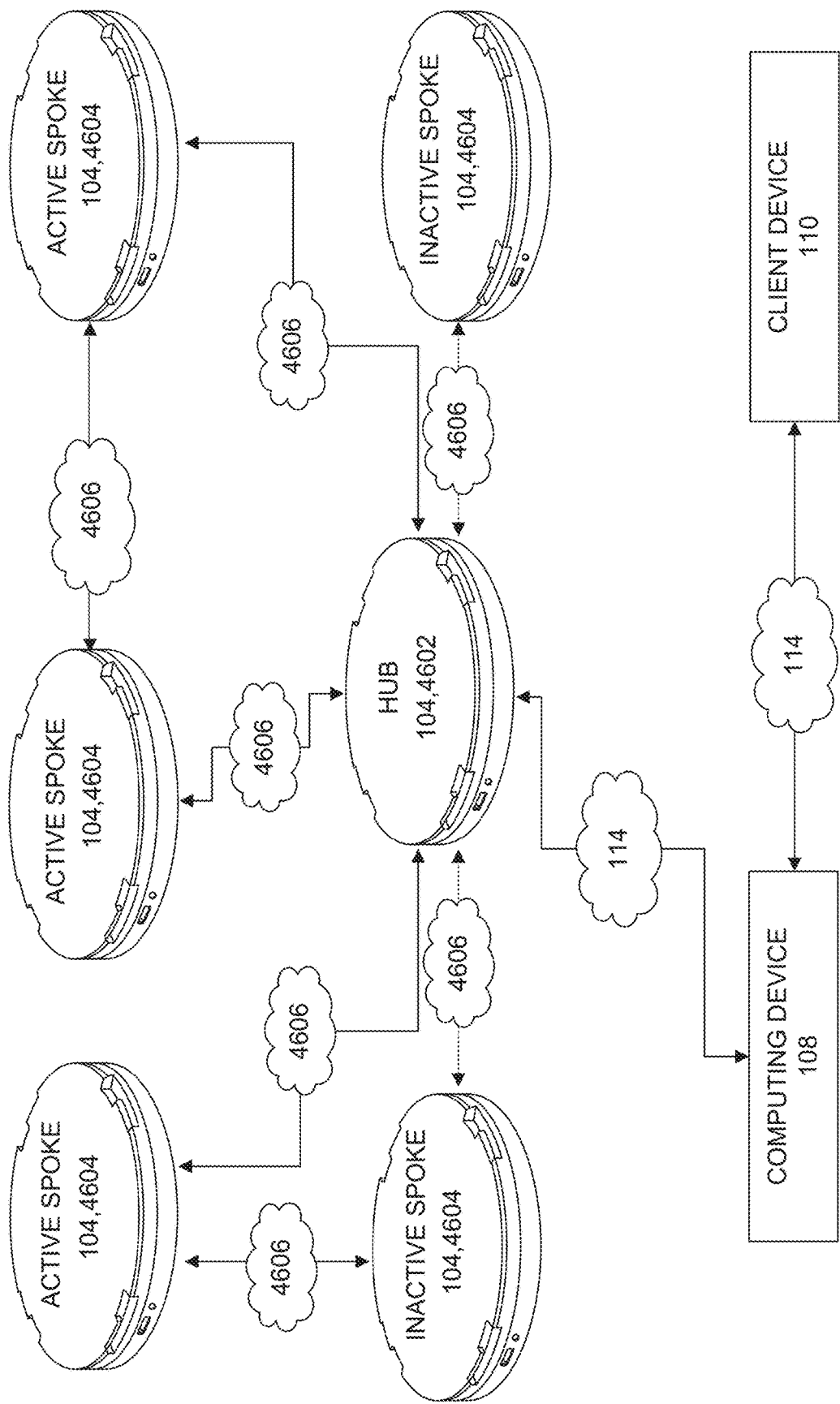
FIG. 46 illustrates a hub and spoke architecture for multiple measuring devices.

FIG. 46 illustrates a hub and spoke architecture for multiple measuring devices 104. The hub and spoke architecture includes a hub measuring device 4602 (also referred to as a hub) and multiple spoke measuring devices 4604 (also referred to as spokes). The hub 4602 may be connected to each spoke 4604 via a communication network 4606 that can be different from the communication network 114. For example, the communication network 4606 can be a local area network servicing a single location (e.g. a single building), and the communication network 114 can be the internet. In some implementations, the network 4606 can be any low-rate personal area network, operation of which may be defined by the technical standard IEEE 802.15.4. In few implementations, the communication any network can be a Bluetooth network. The hub 4602 communicates with external systems (e.g. computing device 108) via a communication network 114 such as the internet.

The spokes 4604 communicate directly with the hub 4602, but may not communicate directly with the computing device 108 and may not be connected to the communication network 114. In some implementations, at least some (e.g. some or all) of the spokes 4604 may communicate with one or more other spokes 4604 via the communication network 4606.

Because only the hub is in communication with external systems (e.g. computing device 108), the hub and spoke architecture is simple and easy to implement, and can reduce complexity, cost and risk. The hub and spoke architecture may allow addition of new spokes at any time, including after the hub 4602 and earlier spokes 4604 have been operable, thereby making the architecture scalable.

The spokes 4604 may include active spokes and passive spokes. The active spokes are spokes 4604 that are currently, or since recently (e.g. since a preset amount of time ago), communicating with the hub 4602. The inactive spokes are spokes 4604 that are currently, or since recently (e.g. since a preset amount of time ago), not communicating with the hub 4602. In some implementations, the hub 4602 may constantly maintain the connection through the communication network 4606 only with the active spokes 4604, but may establish connection with the inactive spokes 4604 through the communication network 4606 only at preset intervals of times. Connecting with the inactive spokes 4604 through the communication network 4606 only at preset intervals of times can preserve bandwidth and/or power by avoiding the need to maintain a constant connection with the inactive spokes 4604.

Although each measuring device 104 is shown in the form of a coaster, in some implementations, any measuring device 104 in the hub and spoke architecture may have any form (e.g. coaster, combination of tray and coaster, combination of container and coaster, and/or the like). In certain implementations, different measuring devices 104 may together be a part of the hub and spoke architecture.

Figure 47:
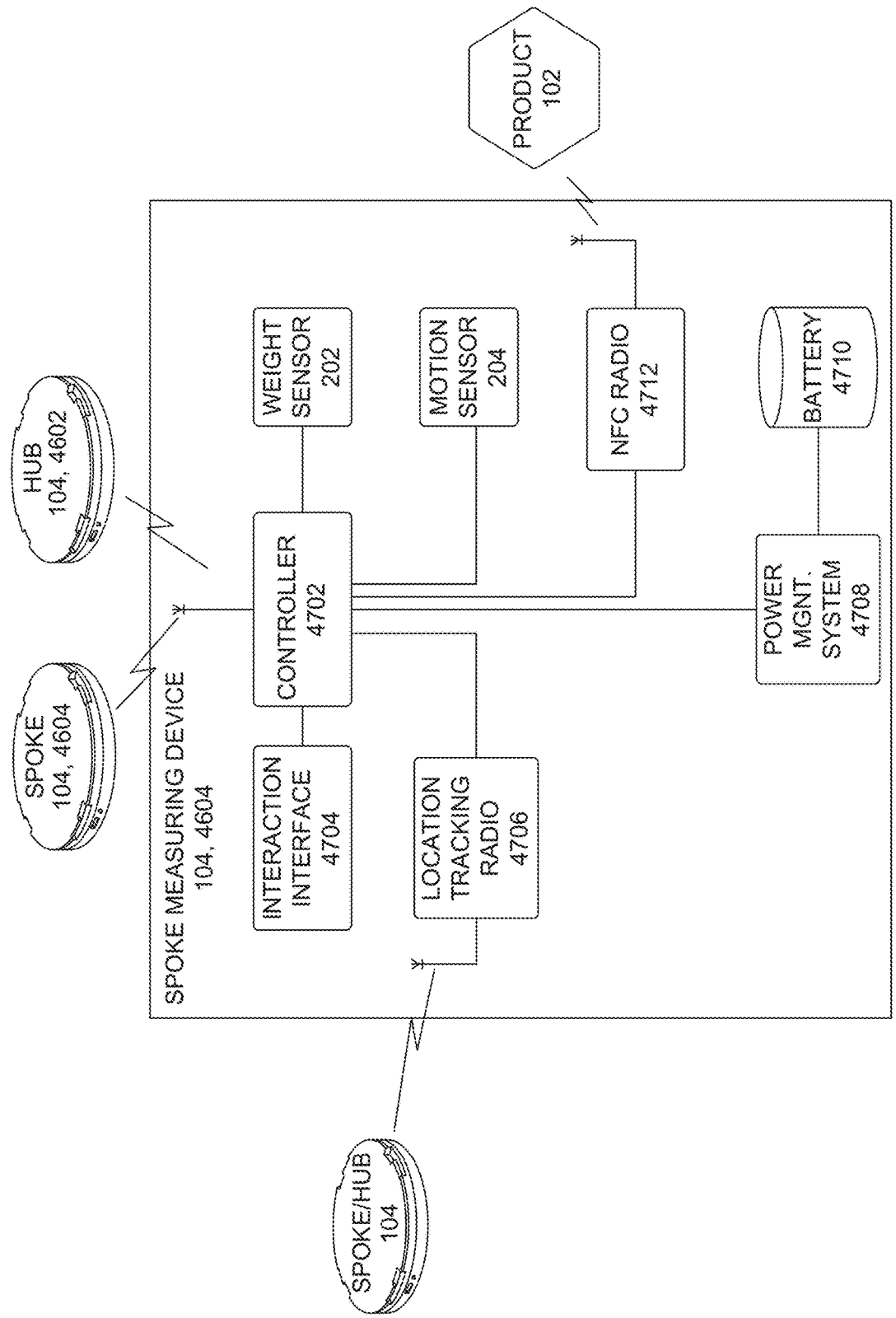
FIG. 47 illustrates an example architecture for a measuring device configured to act like a spoke within the hub and spoke architecture of FIG. 46.

FIG. 47 illustrates an example architecture for a measuring device 104 configured to act like a spoke 4604 within the hub and spoke architecture of FIG. 46. The spoke 4604 can include a controller 4702, an interaction interface 4704, a location tracking radio 4706, a power management system 4708, a battery 4710, a weight sensor 202, a motion sensor 204, and a near field communication (NFC) radio 4712. The controller 4702 can include a radio to communicate with other measuring devices 104, which may be connected with the spoke 4604 in a hub and spoke architecture. The controller 4702 can perform various operations. In some implementations, the functionality of the controller 4702 can be established and/or modified remotely by the computing device 108, which can be a cloud computing system.

Figure 48:
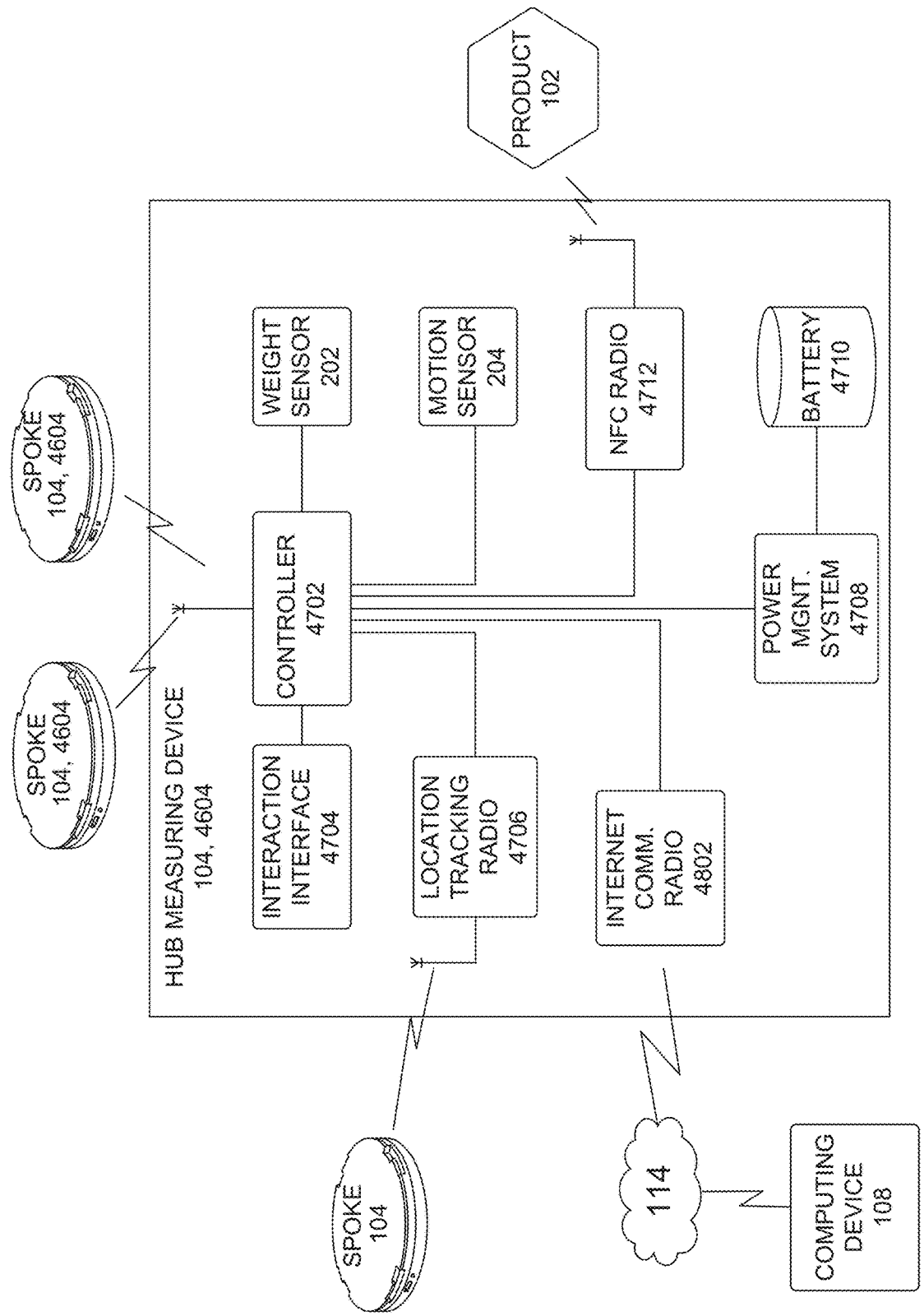
FIG. 48 illustrates an example architecture for a measuring device configured to act like a hub within the hub and spoke architecture of FIG. 46

FIG. 48 illustrates an architecture for a measuring device 104 configured to act like a hub 4602 within the hub and spoke architecture of FIG. 46. In addition to the components described above with respect to FIG. 47, the hub 4602 can include an internet communication radio 4802 that can communicate via the internet 114 to the computing device 108. Although internet is described, in some implementations any other communication network 114 may be there and the communication radio 4802 may be configured for that communication network 114.

Example Computer System

Figure 49:
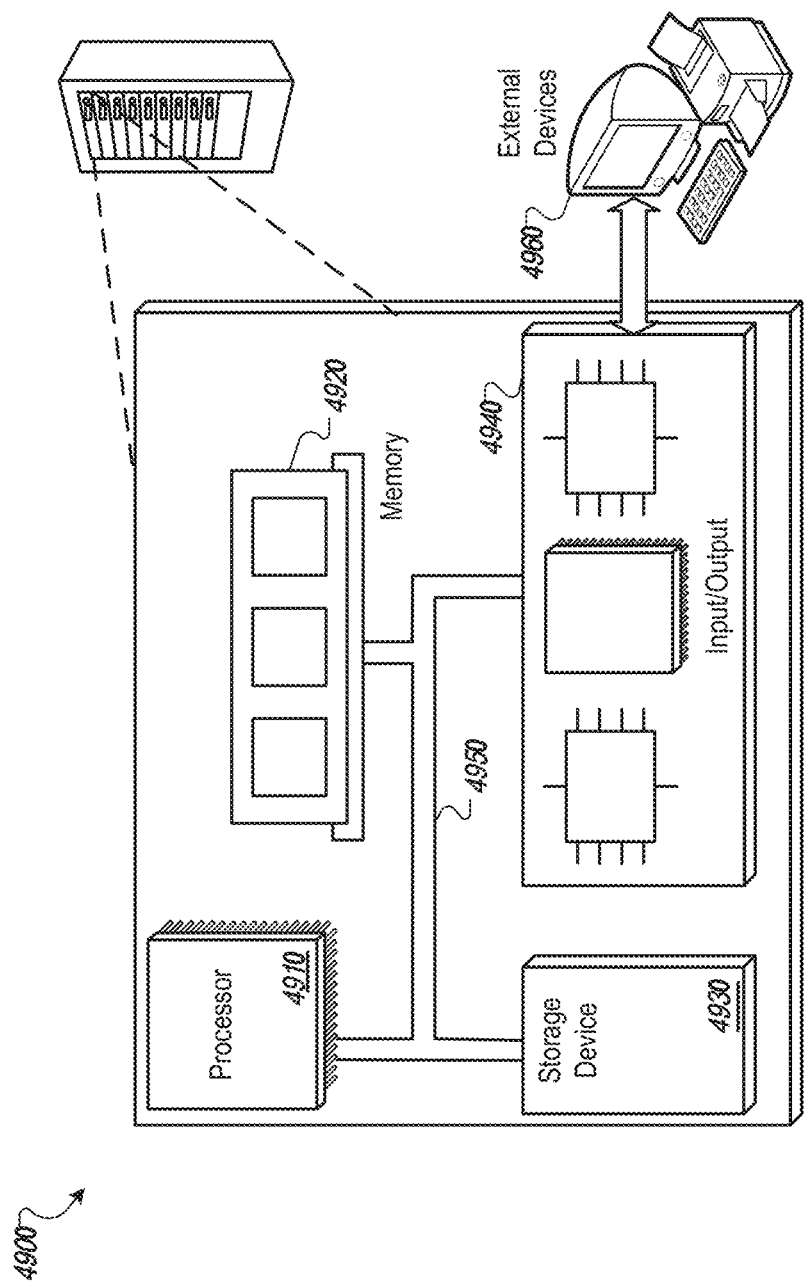
FIG. 49 is a block diagram of an example computer system that can be used to perform operations described above herein.

FIG. 49 is a block diagram of an example computer system 4900 (which, in some examples, can be one or more computing components within the system 100, such as the measuring device 104, the communication device 106, the computing device 108, the client device 110, and/or any other one or more computing components) that can be used to perform operations described above, according to some implementations described herein. The system 4900 includes a processor 4910, a memory 4920, a storage device 4930, and an input/output device 4940. Each of the components 4910, 4920, 4930, and 4940 can be interconnected, for example, using a system bus 4950. The processor 4910 is capable of processing instructions for execution within the system 4900. In some implementations, the processor 4910 is a single-threaded processor. In another implementation, the processor 4910 is a multi-threaded processor. The processor 4910 is capable of processing instructions stored in the memory 4920 or on the storage device 4930.

The memory 4920 stores information within the system 4900. In one implementation, the memory 4920 is a computer-readable medium. In some implementations, the memory 4920 is a volatile memory unit. In another implementation, the memory 4920 is a non-volatile memory unit.

The storage device 4930 is capable of providing mass storage for the system 4900. In some implementations, the storage device 4930 is a computer-readable medium. In various different implementations, the storage device 4930 can include, for example, a hard disk device, an optical disk device, a storage device that is shared over a network by multiple computing devices (e.g., a cloud storage device), or some other large capacity storage device.

The input/output device 4940 provides input/output operations for the system 4900. In some implementations, the input/output device 4940 can include one or more of a network interface devices, e.g., an Ethernet card, a serial communication device, e.g., and RS-232 port, and/or a wireless interface device, e.g., and 802.11 card. In another implementation, the input/output device can include driver devices configured to receive input data and send output data to external devices 4960, e.g., keyboard, printer and display devices. Other implementations, however, can also be used, such as mobile computing devices, mobile communication devices, set-top box television client devices, etc.

Although an example processing system has been described in FIG. 49, implementations of the subject matter and the functional operations described in this specification can be implemented in other types of digital electronic circuitry, or in computer software, firmware, or hardware, including the structures disclosed in this specification and their structural equivalents, or in combinations of one or more of them.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage media (or medium) for execution by, or to control the operation of, data processing apparatus. Alternatively, or in addition, the program instructions can be encoded on an artificially-generated propagated signal—e.g., a machine-generated electrical, optical, or electromagnetic signal—that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The term module, as noted herein, can include software instructions and codes to perform a designated task or a function. A module as used herein can be a software module or a hardware module. A software module can be a part of a computer program, which can include multiple independently developed modules that can be combined or linked via a linking module. A software module can include one or more software routines. A software routine is computer readable code that performs a corresponding procedure or function. A hardware module can be a self-contained component with an independent circuitry that can perform various operations described herein.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any innovations or of what may be claimed, but rather as descriptions of features specific to particular implementations of particular innovations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A device for receiving a consumer product, comprising:
a sensor module for sensing a change in the consumer product corresponding to the use of the consumer product, the sensor module comprising a time sensor configured to observe a time at which the consumer product is used and generate time consumed data based on the observed time; and
a communication module in communication with the sensor, the communication module configured to wirelessly transmit data about the use of the consumer product from the sensor module based on the sensed changes in the consumer product, the data comprising the time consumed data,
wherein the consumer product is selected from the group consisting of a consumer packaged good (CPG), a fast moving consumer good (FMCG), and a food & beverage (F&B).

2. The device of claim 1, wherein the sensor module comprises a weight sensor.

3. The device of claim 1, wherein the sensor module comprises a motion sensor.

4. The device of claim 1, wherein the time consumed data comprises data selected from the group consisting of: a time at which the consumer product is moved, a length of time of a movement of the consumer product, and a time at which the device weighs the consumer product.

5. The device of claim 1, wherein the sensor module comprises one or more sensors selected from the group consisting of: a temperature sensor, a proximity sensor, an infrared sensor, an ultrasonic sensor, a location sensor, a humidity sensor, a tilt sensor, a level sensor, and a touch sensor.

6. The device of claim 1, wherein the communication module comprises a module selected from the group consisting of a Wi-Fi module, a Bluetooth module, a Bluetooth Low Energy module, and a SIM module.

7. The device of claim 1, wherein the device is in the form of a coaster.

8. The device of claim 1, wherein the device is in the form of a tray.

9. The device of claim 1, further comprising a connector for attaching the device to a consumer product during use of the consumer product.

10. The device of claim 1, wherein the connector comprises a magnet, a hook and loop connector, or double-sided tape.

11. The device of claim 1, further comprising a local storage module configured to store the data.

12. The device of claim 1, further comprising a battery configured to supply electrical power to the device.

13. A system, comprising:
a computing device; and
the device of claim 1 in communication with the computing device via a communication network and configured to transmit the data about the use of the consumer product to the computing device,
wherein the computing device is configured to generate a report based on the data about the use of the consumer product.

14. The system of claim 13, wherein the report comprises qualitative and quantitative insights about the use of the consumer product.

15. The system of claim 14, further comprising one or more additional devices each associated with a respective different consumer product, each of the one or more additional devices being in communication with the computing device.

16. The device of claim 1, wherein generating the time consumed data comprises generating a timestamp for the usage of the product.

17. The device of claim 16, wherein the timestamp comprises morning, afternoon, evening, and night.

18. The device of claim 16, wherein the timestamp comprises real-time usage of the product.

* * * * *